US012268422B2

(12) United States Patent
Hua

(10) Patent No.: US 12,268,422 B2
(45) Date of Patent: Apr. 8, 2025

(54) SYSTEMS, DEVICES AND METHODS FOR TREATING A LATERAL CURVATURE OF A SPINE

(71) Applicant: SPINE23 INC., Campbell, CA (US)

(72) Inventor: Sherwin Hua, Campbell, CA (US)

(73) Assignee: SPINE23 INC., Campbell, CA (US)

(*) Notice: Subject to any disclaimer, the term of this patent is extended or adjusted under 35 U.S.C. 154(b) by 253 days.

(21) Appl. No.: 17/779,975

(22) PCT Filed: Nov. 25, 2020

(86) PCT No.: PCT/US2020/062420
§ 371 (c)(1),
(2) Date: May 25, 2022

(87) PCT Pub. No.: WO2021/108709
PCT Pub. Date: Jun. 3, 2021

(65) Prior Publication Data
US 2022/0409246 A1 Dec. 29, 2022

Related U.S. Application Data

(60) Provisional application No. 62/941,641, filed on Nov. 27, 2019.

(51) Int. Cl.
A61B 17/70 (2006.01)
A61B 90/00 (2016.01)

(52) U.S. Cl.
CPC ...... A61B 17/7052 (2013.01); A61B 17/7032 (2013.01); A61B 2090/064 (2016.02); A61B 2090/065 (2016.02); A61B 2090/066 (2016.02)

(58) Field of Classification Search
None
See application file for complete search history.

(56) References Cited

U.S. PATENT DOCUMENTS 4,448,191 A 5/1984 Rodnyansky et al.
5,092,866 A 3/1992 Breard et al.
(Continued)

FOREIGN PATENT DOCUMENTS

CN 2782035 Y 5/2006
CN 1972639 A 5/2007
(Continued)

OTHER PUBLICATIONS

U.S. Appl. No. 13/098,325 (U.S. Pat. No. 8,545,541), filed Apr. 29, 2011, System and Method for Wire-Guided Pedicle Screw Stabilization of Spinal Vertebrae.
(Continued)

Primary Examiner — Eduardo C Robert
Assistant Examiner — Michelle C Green
(74) Attorney, Agent, or Firm — Knobbe Martens Olson & Bear LLP

(57) ABSTRACT

A system for correcting a lateral curvature of a spine that can include a plurality of screws configured to be implanted in a plurality of vertebrae, and a plurality of extensions configured to be removably coupled with the plurality of screws. Some embodiments of the plurality of extensions can be curved, bent, angled, and/or offset along at least a portion thereof and can be removably coupled with a screw head of each of the plurality of screws. The system can include a connecting element or rod that is configured to be coupled with the plurality of screw heads. Some embodiments of the system can be configured such that the rod can be guided along the plurality of extensions from the proximal toward the distal end portions of the extensions and into engagement with the plurality of screws to cause the plurality of vertebrae to move laterally.

29 Claims, 14 Drawing Sheets

(56) References Cited

U.S. PATENT DOCUMENTS

| | | |
|---|---|---|
| 5,242,443 A | 9/1993 | Kambin |
| 5,300,076 A | 4/1994 | Leriche |
| 5,306,275 A | 4/1994 | Bryan |
| 5,324,316 A | 6/1994 | Schulman et al. |
| 5,411,546 A | 5/1995 | Bowald et al. |
| 5,531,779 A | 7/1996 | Dahl et al. |
| 5,672,175 A | 9/1997 | Martin |
| 5,728,097 A | 3/1998 | Mathews |
| 5,865,842 A | 2/1999 | Knuth et al. |
| 5,938,689 A | 8/1999 | Fischell et al. |
| 5,975,085 A | 11/1999 | Rise |
| 5,980,521 A | 11/1999 | Montague et al. |
| 6,011,991 A | 1/2000 | Mardirossian |
| 6,016,449 A | 1/2000 | Fischell et al. |
| 6,051,017 A | 4/2000 | Loeb et al. |
| 6,090,113 A | 7/2000 | Le Couedic et al. |
| 6,175,764 B1 | 1/2001 | Loeb et al. |
| 6,176,242 B1 | 1/2001 | Rise |
| 6,181,965 B1 | 1/2001 | Loeb et al. |
| 6,185,452 B1 | 2/2001 | Schulman et al. |
| 6,208,881 B1 | 3/2001 | Champeau |
| 6,208,894 B1 | 3/2001 | Schulman et al. |
| 6,214,016 B1 | 4/2001 | Williams et al. |
| 6,227,203 B1 | 5/2001 | Rise et al. |
| 6,235,028 B1 | 5/2001 | Brumfield et al. |
| 6,240,316 B1 | 5/2001 | Richmond et al. |
| 6,263,237 B1 | 7/2001 | Rise |
| 6,343,226 B1 | 1/2002 | Sunde et al. |
| 6,427,086 B1 | 7/2002 | Fischell et al. |
| 6,445,953 B1 | 9/2002 | Bulkes et al. |
| 6,482,182 B1 | 11/2002 | Carroll et al. |
| 6,485,491 B1 | 11/2002 | Farris et al. |
| 6,493,592 B1 | 12/2002 | Leonard et al. |
| 6,530,929 B1 | 3/2003 | Justis et al. |
| 6,546,277 B1 | 4/2003 | Franck et al. |
| 6,549,810 B1 | 4/2003 | Leonard et al. |
| 6,582,441 B1 | 6/2003 | He et al. |
| 6,597,954 B1 | 7/2003 | Pless et al. |
| 6,622,051 B1 | 9/2003 | Bishay et al. |
| 6,623,490 B1 | 9/2003 | Crane et al. |
| 6,665,562 B2 | 12/2003 | Gluckman |
| 6,711,430 B1 | 3/2004 | Ferris et al. |
| 6,731,976 B2 | 5/2004 | Penn et al. |
| 6,735,475 B1 | 5/2004 | Whitehurst et al. |
| 6,764,498 B2 | 7/2004 | Mische |
| 6,782,292 B2 | 8/2004 | Whitehurst |
| 6,788,975 B1 | 9/2004 | Whitehurst et al. |
| 6,793,656 B1 | 9/2004 | Mathews |
| 6,795,737 B2 | 9/2004 | Gielen et al. |
| 6,819,956 B2 | 11/2004 | DiLorenzo |
| 6,830,544 B2 | 12/2004 | Tanner |
| 6,862,479 B1 | 3/2005 | Whitehurst et al. |
| 6,871,098 B2 | 3/2005 | Nuttin |
| 6,916,320 B2 | 7/2005 | Michelson |
| 6,922,590 B1 | 7/2005 | Whitehurst |
| 6,929,606 B2 | 8/2005 | Ritland |
| 6,950,707 B2 | 9/2005 | Whitehurst |
| 6,959,215 B2 | 10/2005 | Gliner et al. |
| 6,970,741 B1 | 11/2005 | Whitehurst et al. |
| 6,978,180 B2 | 12/2005 | Tadlock |
| 6,990,377 B2 | 1/2006 | Gliner et al. |
| 7,003,352 B1 | 2/2006 | Whitehurst |
| 7,006,859 B1 | 2/2006 | Osorio et al. |
| 7,008,422 B2 | 3/2006 | Foley et al. |
| 7,011,660 B2 | 3/2006 | Sherman et al. |
| 7,013,177 B1 | 3/2006 | Whitehurst et al. |
| 7,063,708 B2 | 6/2006 | Gibson et al. |
| 7,063,725 B2 | 6/2006 | Foley |
| 7,066,961 B2 | 6/2006 | Michelson |
| 7,083,621 B2 | 8/2006 | Shaolian et al. |
| 7,103,408 B2 | 9/2006 | Haller et al. |
| 7,107,103 B2 | 9/2006 | Schulman et al. |
| 7,146,217 B2 | 12/2006 | Firlik et al. |
| 7,150,737 B2 | 12/2006 | Purdy et al. |
| 7,151,961 B1 | 12/2006 | Whitehurst et al. |
| 7,158,333 B1 | 1/2007 | Ardja et al. |
| 7,167,751 B1 | 1/2007 | Whitehurst et al. |
| 7,174,212 B1 | 2/2007 | Klehn et al. |
| 7,179,225 B2 | 2/2007 | Shluzs et al. |
| 7,179,261 B2 | 2/2007 | Seivol et al. |
| 7,187,967 B2 | 3/2007 | Kennedy |
| 7,188,626 B2 | 3/2007 | Foley et al. |
| 7,209,787 B2 | 4/2007 | Dilorenzo |
| 7,221,981 B2 | 5/2007 | Gliner |
| 7,236,830 B2 | 6/2007 | Gliner |
| 7,236,831 B2 | 6/2007 | Firlik et al. |
| 7,250,052 B2 | 7/2007 | Landry et al. |
| 7,255,686 B2 | 8/2007 | Putz |
| 7,277,758 B2 | 10/2007 | DiLorenzo |
| 7,282,064 B2 | 10/2007 | Chin |
| 7,283,856 B2 | 10/2007 | Boling |
| 7,292,890 B2 | 11/2007 | Whitehurst et al. |
| 7,295,875 B2 | 11/2007 | Wallace et al. |
| 7,299,096 B2 | 11/2007 | Balzer et al. |
| 7,302,298 B2 | 11/2007 | Lowry et al. |
| 7,305,268 B2 | 12/2007 | Gliner et al. |
| 7,306,603 B2 | 12/2007 | Boehm, Jr. et al. |
| 7,326,210 B2 | 2/2008 | Jahng et al. |
| D565,735 S | 4/2008 | Washbon |
| 7,353,064 B2 | 4/2008 | Gliner et al. |
| 7,376,468 B2 | 5/2008 | King et al. |
| 7,386,350 B2 | 6/2008 | Villims |
| 7,406,105 B2 | 7/2008 | Delmain et al. |
| 7,440,806 B1 | 10/2008 | Whitehurst et al. |
| 7,465,306 B2 | 12/2008 | Pond, Jr. et al. |
| 7,468,064 B2 | 12/2008 | Bruneau et al. |
| 7,491,208 B2 | 2/2009 | Pond, Jr. et al. |
| 7,491,218 B2 | 2/2009 | Landry et al. |
| 7,493,171 B1 | 2/2009 | Whitehurst et al. |
| 7,497,869 B2 | 3/2009 | Justis |
| 7,515,961 B2 | 4/2009 | Germanson et al. |
| 7,520,879 B2 | 4/2009 | Justis et al. |
| 7,527,638 B2 | 5/2009 | Anderson et al. |
| 7,547,318 B2 | 6/2009 | Birkmeyer et al. |
| 7,575,581 B2 | 8/2009 | Lovell |
| 7,588,575 B2 | 9/2009 | Colleran et al. |
| 7,588,588 B2 | 9/2009 | Spitler et al. |
| 7,604,658 B2 | 10/2009 | Wilson et al. |
| 7,666,189 B2 | 2/2010 | Gerber et al. |
| 7,684,867 B2 | 3/2010 | Jaax et al. |
| 7,686,814 B2 | 3/2010 | Lim et al. |
| 7,691,132 B2 | 4/2010 | Landry et al. |
| 7,708,763 B2 | 5/2010 | Selover et al. |
| 7,717,944 B2 | 5/2010 | Foley et al. |
| 7,725,196 B2 | 5/2010 | Machado et al. |
| 7,736,370 B2 | 6/2010 | Sweeney |
| 7,749,233 B2 | 7/2010 | Farr et al. |
| 7,758,584 B2 | 7/2010 | Bankoski et al. |
| 7,758,617 B2 | 7/2010 | Iott et al. |
| 7,763,055 B2 | 7/2010 | Foley |
| 7,776,051 B2 | 8/2010 | Colleran et al. |
| 7,824,410 B2 | 11/2010 | Simonson et al. |
| 7,846,093 B2 | 12/2010 | Gorek et al. |
| 7,875,031 B2 | 1/2011 | Chin et al. |
| 7,894,912 B2 | 2/2011 | Benabid et al. |
| 7,917,230 B2 | 3/2011 | Bly |
| 7,937,160 B2 | 5/2011 | Garabedian et al. |
| 7,947,045 B2 | 5/2011 | Hestad et al. |
| 7,955,355 B2 | 6/2011 | Chin |
| 7,974,696 B1 | 7/2011 | DiLorenzo |
| 7,991,465 B2 | 8/2011 | Bartic et al. |
| 8,000,795 B2 | 8/2011 | Lozano |
| 8,043,343 B2 | 10/2011 | Miller et al. |
| 8,052,711 B2 | 11/2011 | Hanse et al. |
| 8,052,720 B2 | 11/2011 | Kuester et al. |
| 8,060,207 B2 | 11/2011 | Wallace et al. |
| 8,075,565 B2 | 12/2011 | Wilcox et al. |
| 8,103,350 B2 | 1/2012 | Wallace et al. |
| 8,150,524 B2 | 4/2012 | Maschino et al. |
| 8,209,027 B2 | 6/2012 | Butson et al. |
| 8,216,173 B2 | 7/2012 | Dacey, Jr. et al. |
| 8,216,282 B2 | 7/2012 | Hua |
| 8,282,593 B2 | 10/2012 | Dacey, Jr. et al. |
| 8,333,753 B2 | 12/2012 | Nishtala |

(56) References Cited

U.S. PATENT DOCUMENTS

| | | |
|---|---|---|
| 8,333,770 B2 | 12/2012 | Hua |
| 8,343,086 B2 | 1/2013 | Dacey, Jr. et al. |
| 8,346,365 B2 | 1/2013 | Lozano |
| 8,366,652 B2 | 2/2013 | Dacey, Jr. et al. |
| 8,366,714 B2 | 2/2013 | Jones et al. |
| 8,401,654 B1 | 3/2013 | Foster et al. |
| 8,417,345 B2 | 4/2013 | Machado et al. |
| 8,515,541 B1 | 8/2013 | Jaax et al. |
| 8,515,542 B2 | 8/2013 | Jaax et al. |
| 8,545,541 B2 | 10/2013 | Hua |
| 8,556,940 B2 | 10/2013 | Hua |
| 8,706,181 B2 | 4/2014 | Stypulkowski et al. |
| 8,721,691 B2 | 5/2014 | Hua |
| 8,731,674 B2 | 5/2014 | Wallace |
| 8,798,754 B2 | 8/2014 | Knudson et al. |
| 9,179,875 B2 | 11/2015 | Hua |
| 9,198,698 B1 | 12/2015 | Doose et al. |
| 9,307,925 B2 | 4/2016 | Russell et al. |
| 9,327,069 B2 | 5/2016 | Foster et al. |
| 9,352,145 B2 | 5/2016 | Whitehurst et al. |
| 9,402,661 B2 * | 8/2016 | Reitblat ............... A61B 17/708 |
| 9,421,373 B2 | 8/2016 | DiLorenzo |
| 9,630,019 B2 | 4/2017 | Valente et al. |
| 9,642,552 B2 | 5/2017 | Hua |
| 9,724,515 B2 | 8/2017 | Fostick et al. |
| 9,820,668 B2 | 11/2017 | Hua |
| 9,867,978 B1 | 1/2018 | Rapoport et al. |
| 9,877,846 B2 | 1/2018 | Dvorak et al. |
| 9,919,146 B2 | 3/2018 | Hua |
| 9,919,148 B2 | 3/2018 | Howard et al. |
| 9,925,376 B2 | 3/2018 | Hartig et al. |
| 10,004,543 B2 | 6/2018 | Stokes et al. |
| 10,194,960 B1 | 2/2019 | Hammann et al. |
| 10,406,351 B2 | 9/2019 | Hua |
| 10,660,631 B1 | 5/2020 | Boesel et al. |
| 10,702,314 B2 | 7/2020 | Reitblat et al. |
| 10,736,533 B2 | 8/2020 | Hua |
| 10,973,551 B2 | 4/2021 | Hua |
| 11,160,580 B2 | 11/2021 | Hua |
| 11,759,238 B2 | 9/2023 | Hua |
| 2001/0003156 A1 | 6/2001 | Gill |
| 2002/0151770 A1 | 10/2002 | Noll, III et al. |
| 2003/0028072 A1 | 2/2003 | Fischell et al. |
| 2003/0040753 A1 | 2/2003 | Daum et al. |
| 2003/0088245 A1 | 5/2003 | Woloszko et al. |
| 2003/0093129 A1 | 5/2003 | Nicolelis et al. |
| 2003/0135147 A1 | 7/2003 | Rosenberg et al. |
| 2003/0171750 A1 | 9/2003 | Chin |
| 2003/0208203 A1 | 11/2003 | Lim et al. |
| 2003/0233125 A1 | 12/2003 | Kaplan et al. |
| 2003/0233126 A1 | 12/2003 | Kaplan et al. |
| 2004/0030236 A1 | 2/2004 | Mazzochi et al. |
| 2004/0082961 A1 | 4/2004 | Teitelbaum |
| 2004/0088024 A1 | 5/2004 | Firlik et al. |
| 2004/0147928 A1 | 7/2004 | Landry et al. |
| 2004/0186532 A1 | 9/2004 | Tadlock |
| 2004/0225335 A1 | 11/2004 | Whitehurst et al. |
| 2004/0243130 A1 | 12/2004 | Biscup |
| 2004/0243207 A1 | 12/2004 | Olson et al. |
| 2004/0267274 A1 | 12/2004 | Patel et al. |
| 2005/0021040 A1 | 1/2005 | Bertagnoli |
| 2005/0049649 A1 | 3/2005 | Luders et al. |
| 2005/0075680 A1 | 4/2005 | Lowry et al. |
| 2005/0101954 A1 | 5/2005 | Simonson |
| 2005/0102006 A1 | 5/2005 | Whitehurst et al. |
| 2005/0131311 A1 | 6/2005 | Leuthardt et al. |
| 2005/0131422 A1 | 6/2005 | Anderson et al. |
| 2005/0137646 A1 | 6/2005 | Wallace et al. |
| 2005/0137652 A1 | 6/2005 | Cauller et al. |
| 2005/0182453 A1 | 8/2005 | Whitehurst et al. |
| 2005/0192570 A1 | 9/2005 | Jackson |
| 2005/0192589 A1 | 9/2005 | Raymond et al. |
| 2005/0203599 A1 | 9/2005 | Garabedian et al. |
| 2005/0228380 A1 | 10/2005 | Moore et al. |
| 2005/0245969 A1 | 11/2005 | Loeb |
| 2005/0251237 A1 | 11/2005 | Kuzma et al. |
| 2005/0283203 A1 | 12/2005 | Flaherty et al. |
| 2006/0005845 A1 | 1/2006 | Karr et al. |
| 2006/0025841 A1 | 2/2006 | McIntyre |
| 2006/0030872 A1 | 2/2006 | Culbert et al. |
| 2006/0058854 A1 | 3/2006 | Abrams et al. |
| 2006/0089652 A1 | 4/2006 | Eckman |
| 2006/0095035 A1 | 5/2006 | Jones et al. |
| 2006/0111767 A1 | 5/2006 | Olson et al. |
| 2006/0173522 A1 | 8/2006 | Osorio |
| 2006/0184143 A1 | 8/2006 | Jolly et al. |
| 2006/0195154 A1 | 8/2006 | Jaax et al. |
| 2006/0206165 A1 | 9/2006 | Jaax et al. |
| 2006/0212087 A1 | 9/2006 | Haller et al. |
| 2006/0212090 A1 | 9/2006 | Lozano et al. |
| 2006/0212091 A1 | 9/2006 | Lozano et al. |
| 2006/0234279 A1 | 10/2006 | Miller et al. |
| 2006/0235279 A1 | 10/2006 | Hawkes et al. |
| 2006/0241600 A1 | 10/2006 | Ensign et al. |
| 2006/0241717 A1 | 10/2006 | Whitehurst et al. |
| 2006/0264942 A1 | 11/2006 | Lim et al. |
| 2006/0264962 A1 | 11/2006 | Chin et al. |
| 2007/0016188 A1 | 1/2007 | Boehm, Jr. et al. |
| 2007/0016198 A1 | 1/2007 | Boehm, Jr. et al. |
| 2007/0016199 A1 | 1/2007 | Boehm, Jr. et al. |
| 2007/0021800 A1 | 1/2007 | Whitehurst et al. |
| 2007/0027498 A1 | 2/2007 | Maschino et al. |
| 2007/0032718 A1 | 2/2007 | Shults et al. |
| 2007/0032839 A1 | 2/2007 | Parramon et al. |
| 2007/0060974 A1 | 3/2007 | Lozano |
| 2007/0078460 A1 | 4/2007 | Frigg et al. |
| 2007/0078503 A1 | 4/2007 | Kuzma et al. |
| 2007/0088417 A1 | 4/2007 | Schouenborg |
| 2007/0093814 A1 | 4/2007 | Callahan, II et al. |
| 2007/0100393 A1 | 5/2007 | Whitehurst et al. |
| 2007/0106143 A1 | 5/2007 | Flaherty |
| 2007/0123954 A1 | 5/2007 | Gielen et al. |
| 2007/0135867 A1 | 6/2007 | Klosterman et al. |
| 2007/0167954 A1 | 7/2007 | Sicvol et al. |
| 2007/0173733 A1 | 7/2007 | Le et al. |
| 2007/0191840 A1 | 8/2007 | Pond, Jr. et al. |
| 2007/0219554 A1 | 9/2007 | Landry et al. |
| 2007/0219854 A1 | 9/2007 | Mueller et al. |
| 2007/0233079 A1 | 10/2007 | Fallin et al. |
| 2007/0233097 A1 | 10/2007 | Anderson et al. |
| 2007/0233158 A1 | 10/2007 | Rodriguez |
| 2007/0239159 A1 | 10/2007 | Altarac et al. |
| 2007/0239259 A1 | 10/2007 | Boylan et al. |
| 2007/0265582 A1 | 11/2007 | Kaplan et al. |
| 2007/0265683 A1 | 11/2007 | Ehrlich |
| 2007/0270815 A1 | 11/2007 | Johnson et al. |
| 2007/0282395 A1 | 12/2007 | Maltan et al. |
| 2007/0282396 A1 | 12/2007 | Overstreet et al. |
| 2007/0299443 A1 | 12/2007 | DiPoto et al. |
| 2007/0299444 A1 | 12/2007 | DiPoto et al. |
| 2008/0004676 A1 | 1/2008 | Osypka et al. |
| 2008/0009864 A1 | 1/2008 | Forton et al. |
| 2008/0009920 A1 | 1/2008 | Gibson et al. |
| 2008/0015582 A1 | 1/2008 | DiPoto et al. |
| 2008/0039838 A1 | 2/2008 | Landry et al. |
| 2008/0045957 A1 | 2/2008 | Landry et al. |
| 2008/0046012 A1 | 2/2008 | Covalin et al. |
| 2008/0071274 A1 | 3/2008 | Ensign |
| 2008/0071323 A1 | 3/2008 | Lowry et al. |
| 2008/0077139 A1 | 3/2008 | Landry et al. |
| 2008/0086130 A1 | 4/2008 | Lake et al. |
| 2008/0097457 A1 | 4/2008 | Warnick |
| 2008/0097519 A1 | 4/2008 | Calderon et al. |
| 2008/0119849 A1 | 5/2008 | Beardsley et al. |
| 2008/0119850 A1 | 5/2008 | Sicvol et al. |
| 2008/0119862 A1 | 5/2008 | Wicker et al. |
| 2008/0125788 A1 | 5/2008 | Cohen et al. |
| 2008/0125817 A1 | 5/2008 | Arnett et al. |
| 2008/0140075 A1 | 6/2008 | Ensign et al. |
| 2008/0140120 A1 | 6/2008 | Hestad et al. |
| 2008/0140132 A1 | 6/2008 | Perez-Cruet |
| 2008/0140154 A1 | 6/2008 | Loeb et al. |
| 2008/0177269 A1 | 7/2008 | Seelig |
| 2008/0183241 A1 | 7/2008 | Bedenbaugh |

(56) References Cited

U.S. PATENT DOCUMENTS

| | | |
|---|---|---|
| 2008/0208074 A1 | 8/2008 | Snyder et al. |
| 2008/0208302 A1 | 8/2008 | Alexander et al. |
| 2008/0218472 A1 | 9/2008 | Breen et al. |
| 2008/0262318 A1 | 10/2008 | Gorek et al. |
| 2008/0312716 A1 | 12/2008 | Russell |
| 2009/0018599 A1 | 1/2009 | Hastings et al. |
| 2009/0054955 A1 | 2/2009 | Kopell et al. |
| 2009/0082819 A1 | 3/2009 | Blain et al. |
| 2009/0112278 A1 | 4/2009 | Wingeier et al. |
| 2009/0118804 A1 | 5/2009 | Moffitt et al. |
| 2009/0125080 A1 | 5/2009 | Montgomery |
| 2009/0171392 A1 | 7/2009 | Garcia-Bengochea et al. |
| 2009/0187220 A1 | 7/2009 | Hamada |
| 2009/0216278 A1 | 8/2009 | Song |
| 2009/0221878 A1 | 9/2009 | Gorek |
| 2009/0221879 A1 | 9/2009 | Gorek |
| 2009/0222044 A1 | 9/2009 | Gorek |
| 2009/0222045 A1 | 9/2009 | Gorek |
| 2009/0222046 A1 | 9/2009 | Gorek |
| 2009/0234392 A1 | 9/2009 | Dziedzic et al. |
| 2009/0259137 A1 | 10/2009 | Delic et al. |
| 2009/0287061 A1 | 11/2009 | Feigenbaum et al. |
| 2010/0049206 A1 | 2/2010 | Biyani |
| 2010/0145176 A1 | 6/2010 | Himes |
| 2010/0234792 A1 | 9/2010 | Dacey, Jr. et al. |
| 2010/0234793 A1 | 9/2010 | Dacey, Jr. et al. |
| 2010/0240017 A1 | 9/2010 | Dacey, Jr. et al. |
| 2010/0241048 A1 | 9/2010 | Dacey, Jr. et al. |
| 2010/0241050 A1 | 9/2010 | Dacey, Jr. et al. |
| 2010/0241051 A1 | 9/2010 | Dacey, Jr. et al. |
| 2010/0241052 A1 | 9/2010 | Dacey, Jr. et al. |
| 2010/0241053 A1 | 9/2010 | Dacey, Jr. et al. |
| 2010/0249692 A1 | 9/2010 | Dacey, Jr. et al. |
| 2010/0249844 A1 | 9/2010 | Durrani |
| 2010/0292629 A1 | 11/2010 | Dacey, Jr. et al. |
| 2011/0022088 A1 | 1/2011 | Forton et al. |
| 2011/0077692 A1 | 3/2011 | Jackson |
| 2011/0112590 A1 | 5/2011 | Wu et al. |
| 2011/0172674 A1 | 7/2011 | Bankoski et al. |
| 2011/0196426 A1 | 8/2011 | Peukert et al. |
| 2011/0238117 A1 | 9/2011 | Geist et al. |
| 2011/0301647 A1* | 12/2011 | Hua ............ A61B 17/7032 606/279 |
| 2011/0319938 A1 | 12/2011 | Piza Vallespir et al. |
| 2012/0065693 A1 | 3/2012 | Lim et al. |
| 2013/0184763 A1 | 7/2013 | McClintock et al. |
| 2013/0289385 A1 | 10/2013 | Lozano et al. |
| 2013/0325069 A1 | 12/2013 | Lamo et al. |
| 2014/0039556 A1 | 2/2014 | Rutschmann et al. |
| 2014/0243714 A1 | 8/2014 | Ward et al. |
| 2014/0350612 A1 | 11/2014 | Leroux et al. |
| 2015/0066088 A1 | 3/2015 | Brinkman et al. |
| 2015/0216568 A1 | 8/2015 | Trigueros et al. |
| 2015/0230836 A1* | 8/2015 | Cochran ............ A61B 17/7032 606/86 A |
| 2015/0374354 A1 | 12/2015 | Boyd et al. |
| 2016/0158051 A1 | 6/2016 | Mische |
| 2016/0166326 A1 | 6/2016 | Bakker et al. |
| 2016/0220821 A1 | 8/2016 | O'Connell et al. |
| 2016/0228693 A1 | 8/2016 | Vardiman |
| 2016/0331410 A1 | 11/2016 | Tsuang et al. |
| 2016/0331971 A1 | 11/2016 | Gill |
| 2016/0367809 A1 | 12/2016 | Patel et al. |
| 2017/0143966 A1 | 5/2017 | Reymers et al. |
| 2017/0151436 A1 | 6/2017 | Flaherty et al. |
| 2017/0164985 A1 | 6/2017 | Reitblat et al. |
| 2018/0000372 A1 | 1/2018 | Hua |
| 2018/0070987 A1 | 3/2018 | Su et al. |
| 2019/0069930 A1 | 3/2019 | Su et al. |
| 2019/0090918 A1 | 3/2019 | Jackson |
| 2019/0142470 A1* | 5/2019 | Kim ............ A61B 17/708 606/246 |
| 2019/0216453 A1 | 7/2019 | Predick et al. |
| 2019/0231394 A1 | 8/2019 | Bechtel et al. |
| 2019/0290332 A1 | 9/2019 | Tsuang et al. |
| 2019/0336182 A1* | 11/2019 | Suh ............ A61B 17/7002 |
| 2020/0107865 A1 | 4/2020 | Lu et al. |
| 2021/0000510 A1 | 1/2021 | Hua |
| 2022/0361922 A1 | 11/2022 | Hua et al. |
| 2022/0387080 A1 | 12/2022 | Hua et al. |

FOREIGN PATENT DOCUMENTS

| | | | |
|---|---|---|---|
| CN | 101022848 A | 8/2007 | |
| CN | 201157401 Y | 12/2008 | |
| CN | 102293680 | 12/2011 | |
| CN | 103096820 | 5/2013 | |
| CN | 103930059 | 7/2014 | |
| EP | 1 062 973 A1 | 12/2000 | |
| EP | 2 155 322 A2 | 2/2010 | |
| EP | 2 777 573 A1 | 9/2014 | |
| EP | 2 851 022 A1 | 3/2015 | |
| EP | 3 092 964 A1 | 11/2016 | |
| EP | 2 892 452 B1 | 8/2018 | |
| GB | 2330078 A | 4/1999 | |
| JP | H10-080431 A | 3/1998 | |
| JP | 2005-516697 A | 6/2005 | |
| JP | 2005-324017 A | 11/2005 | |
| JP | 2006-504505 A | 2/2006 | |
| JP | 2007-520319 A | 7/2006 | |
| JP | 2006-518655 A | 8/2006 | |
| JP | 2007-502662 A | 2/2007 | |
| JP | 2007-524463 A | 8/2007 | |
| JP | 2008-509759 A | 4/2008 | |
| JP | 2008-539029 A | 11/2008 | |
| KR | 101703003 B1 * | 2/2017 | ............ A61B 17/70 |
| RU | 2285483 C2 | 10/2006 | |
| SU | 1771717 A1 | 10/1992 | |
| WO | WO 03/005943 A2 | 1/2003 | |
| WO | WO 03/066153 A2 | 8/2003 | |
| WO | WO 2004/041100 A1 | 5/2004 | |
| WO | WO 2004/075768 A2 | 9/2004 | |
| WO | WO 2005/051306 A2 | 6/2005 | |
| WO | WO 2006/015087 A2 | 2/2006 | |
| WO | WO 2006/019723 A2 | 2/2006 | |
| WO | WO 2006/099462 A2 | 9/2006 | |
| WO | WO 2007/002144 A2 | 1/2007 | |
| WO | WO 2008/039247 A2 | 4/2008 | |
| WO | WO 2008/136802 A1 | 11/2008 | |
| WO | WO 2008/149289 A2 | 12/2008 | |
| WO | WO 2010/039817 A2 | 4/2010 | |
| WO | WO 2010/039817 A3 | 7/2010 | |
| WO | WO 2010/085782 A2 | 7/2010 | |
| WO | WO 2010/039817 A4 | 9/2010 | |
| WO | WO 2011/040986 A1 | 4/2011 | |
| WO | WO 2011/084788 A2 | 7/2011 | |
| WO | WO 2011/123580 A1 | 10/2011 | |
| WO | WO 2011/133583 A1 | 10/2011 | |
| WO | WO 2014/159757 A2 | 10/2014 | |
| WO | WO 2017/039762 A1 | 3/2017 | |
| WO | WO 2021/092495 A1 | 5/2021 | |
| WO | WO 2021/108709 A1 | 6/2021 | |
| WO | WO 2022/241140 | 11/2022 | |

OTHER PUBLICATIONS

U.S. Appl. No. 13/246,432 (U.S. Pat. No. 8,216,282), filed Sep. 27, 2011, System and Method for Wire-Guided Pedicle Screw Stabilization of Spinal Vertebrae.

U.S. Appl. No. 13/122,388 (U.S. Pat. No. 8,556,940), filed Apr. 1, 2011, System and Method for Wire-Guided Pedicle Screw Stabilization of Spinal Vertebrae.

U.S. Appl. No. 14/645,167 (U.S. Pat. No. 9,642,552), filed Mar. 11, 2015, Insertion of Medical Devices Through Non-Orthogonal and Orthogonal Trajectories Within the cranium and Methods of Using.

U.S. Appl. No. 15/483,944 (Pub. No. 2018/0000372), filed Apr. 10, 2017, Insertion of Medical Devices Through Non-Orthogonal and Orthogonal Trajectories Within the Cranium and Methods of Using.

U.S. Appl. No. 16/132,161, filed Sep. 14, 2018, Insertion of Medical Devices Through Non-Orthogonal and Orthogonal Trajectories Within the Cranium and Methods of Using.

(56) References Cited

OTHER PUBLICATIONS

U.S. Appl. No. 16/375,722, filed Apr. 4, 2019, Insertion of Medical Devices Through Non-Orthogonal and Orthogonal Trajectories Within the Cranium and Methods of Using.
U.S. Appl. No. 13/318,462 (U.S. Pat. No. 9,179,875), filed Nov. 1, 2011, Insertion of Medical Devices Through Non-Orthogonal and Orthogonal Trajectories Within the Cranium and Methods of Using.
U.S. Appl. No. 14/202,707 (U.S. Pat. No. 9,820,668), filed Mar. 10, 2014, Insertion of Medical Devices Through Non-Orthogonal and Orthogonal Trajectories Within the Cranium and Methods of Using.
U.S. Appl. No. 15/783,954 (U.S. Pat. No. 10,736,533), filed Oct. 13, 2017, Insertion of Medical Devices Through Non-Orthogonal and Orthogonal Trajectories Within the Cranium and Methods of Using.
U.S. Appl. No. 16/905,700, filed Jun. 18, 2020, Insertion of Medical Devices Through Non-Orthogonal and Orthogonal Trajectories Within the Cranium and Methods of Using.
U.S. Appl. No. 13/082,346 (U.S. Pat. No. 8,721,691), filed Apr. 7, 2011, Systems and Methods for Pedicle Screw Stabilization of Spinal Vertebrae.
U.S. Appl. No. 13/189,432 (U.S. Pat. No. 10,973,551), filed Jul. 22, 2011, Systems and Methods for Pedicle Screw Stabilization of Spinal Vertebrae.
U.S. Appl. No. 13/245,227 (U.S. Pat. No. 8,333,770), filed Sep. 26, 2011, Systems and Methods for Pedicle Screw Stabilization of Spinal Vertebrae.
U.S. Appl. No. 17/025,815 (Pub. No. 2021/0000510), filed Sep. 18, 2020, Systems and Methods for Pedicle Screw Stabilization of Spinal Vertebrae.
U.S. Appl. No. 14/266,732 (U.S. Pat. No. 9,919,146), filed Apr. 30, 2014, Methods and Systems for Intraventricular Brain Stimulation.
U.S. Appl. No. 15/891,231 (U.S. Pat. No. 10,406,351), filed Feb. 7, 2018, Methods and Systems for Intraventricular Brain Stimulation.
U.S. Appl. No. 16/516,034, filed Jul. 18, 2019, Methods and Systems for Intraventricular Brain Stimulation.
U.S. Appl. No. 16/855,941 (U.S. Pat. No. 11,160,580), filed Apr. 22, 2020, Systems and Methods for Pedicle Screw Stabilization of Spinal Vertebrae.
U.S. Appl. No. 17/449,611, filed Sep. 30, 2021, Systems and Methods for Pedicle Screw Stabilization of Spinal Vertebrae.
U.S. Appl. No. 17/775,215, filed May 6, 2022, Systems and Methods for Pedicle Screw Stabilization of Spinal Vertebrae.
U.S. Appl. No. 17/779,975, (present application), filed May 25, 2022, Systems, Devices and Methods for Treating a Lateral Curvature of a Spine.
U.S. Appl. No. 17/743,135 (Pub. No. 2022/0361922), filed May 12, 2022, Systems and Methods for Pedicle Screw Stabilization of Spinal Vertebrae.
"Mantis™ Spinal System Surgical Technique", Stryker Spine, Literature No. TLMANST06071, 2006, (Brochure) in 48 pages.
"Mantis® Spinal System Surgical Technique", Stryker Spine, MIMAN-ST-2_Rev-3, 2015, (Brochure) in 48 pages.
2009 K2M Complex Spine Innovations, "Serengeti Minimally Invasive Retractor System, A Simple Approach to Complex Spine", 2 pages, 2009.
2010 K2M Complex Spine Innovations, Mesa Spinal System Lumbar Products for Surgeons Treating Spinal Disorders, 1 page. Downloaded May 6, 2010.
Buchholz, A. et al., "Deformity Correction Through the Use of Reduction Towers: 2-Dimensional Operative Video", Operative Neurosurgery, Aug. 2020, vol. 19, Issue 2, pp. E157-E158.

Buell. T. et al., "Surgical correction of severe adult lumbar scoliosis (major curves ≥ 75°): retrospective analysis with minimum 2-year follow-up", Journal of Neurosurgery Spine, Jun. 2019, vol. 21, pp. 1-14.
Carbunaru, R. et al., "Rechargeable Battery-Powered bion® Microstimulators for Neuromodulation," Proceedings of the 26th Annual International Conference of the IEEE EMBS San Francisco, CA, USA, Sep. 1-5, 2004. 0-7803-B439-3/04/$20.00@2004 IEEE, in 4 pages.
Demura, S. et al., "Influence of Rod Contouring on Rod Strength and Stiffness in Spine Surgery", Orthopedics, Jun. 2015, vol. 38(6), pp. e520-e523.
Ezzyat, Y. et al., "Closed-loop stimulation of temporal cortex rescues functional networks and improves memory", Nature Communications, vol. 9, Feb. 2018, in 8 pages. URL: https://www.nature.com/articles/s41467-017-02753-0.
Giles, Jim, "Electric currents boosts brain power" in Nature, Oct. 26, 2004, in 2 pages.
Hewitt, John, "Rise of the Cyborgs", Extreme Tech, Jan. 14, 2013, in 6 pages. URL: https://www.extremetech.com/extreme/144579-rise-of-the-cyborgs.
Koivisto, A.M. et al., "Poor Cognitive Outcome in Shunt-Responsive Idiopathic Normal Pressure Hydrocephalus", Neurosurgery, Jan. 2013, vol. 72(1), pp. 1-8.
Kokabu, T. et al., "Identification of optimized rod shapes to guide anatomical spinal reconstruction for adolescent thoracic idiopathic scoliosis", Journal of Orthopaedic Research, Jul. 2018, pp. 3219-3224.
Laxton, A. et al., "Deep Brain Stimulation for the Treatment of Alzheimer Disease and Dementias", World Neurosurgery, Sep./Oct. 2013, 80 (3/4), S28.e1-8.
Lindsey, C. et al., "The Effects of Rod Contouring on Spinal Construct Fatigue Strength", Spine, Jul. 2006, vol. 31, Issue 15, pp. 1680-1687.
Loeb, G. et al., "The BION Devices: Injectable Interfaces with Peripheral Nerves and Muscles." Neurosurg Focus. 2006;20(5) © 2006 American Association of Neurological Surgeons Posted Aug. 15, 2006, in 12 pages.
Medtronic CD Horizon® Sextant® II—Rod Insertion System—Surgical Technique, 2010, IRN10910-20-03/0710, in 48 pages.
Medtronic Sofamor Danek METRx™ System Surgical Technique "Minimal Access Spinal Technologies" article, 2004, in 22 pages.
Mims, C., "A Hardware Update for the Human Brain", The Wall Street Journal, Jun. 5, 2017, in 4 pages. URL: https://www.wsj.com/articles/a-hardware-update-for-the-human-brain-1496660400.
Santoni, B.G. et al., "Cortical Bone Trajectory for Lumbar Pedicle Screws", The Spine Journal, 2009, vol. 9, pp. 366-373.
Simonite, Tim. "Brain blanket boosts mind control" in New Scientist. Feb. 15, 2008, posted online, in 3 pages.
Singer, Emily, "Want to Enhance Your Brain Power? Research hints that electrically stimulating the brain can speed learning," MIT Technology Review, Jun. 26, 2008, in 2 pages.
Torres, et al., "Body Fat and Body Weight Reduction Following Hypothalamic Deep Brain Stimulation in Monkeys: an Intraventricular approach", International Journal of Obesity, Feb. 21, 2012, pp. 1537-1544.
International Search Report and Written Opinion dated Apr. 13, 2021, from PCT Application No. PCT/US2020/062420.
U.S. Appl. No. 17/025,815 (U.S. Pat. No. 11,579,238), filed Sep. 18, 2020, Systems and Methods for Pedicle Screw Stabilization of Spinal Vertebrae.
U.S. Appl. No. 17/775,215 (Pub. No. 2022/0387080), filed May 6, 2022, Systems and Methods for Pedicle Screw Stabilization of Spinal Vertebrae.

* cited by examiner

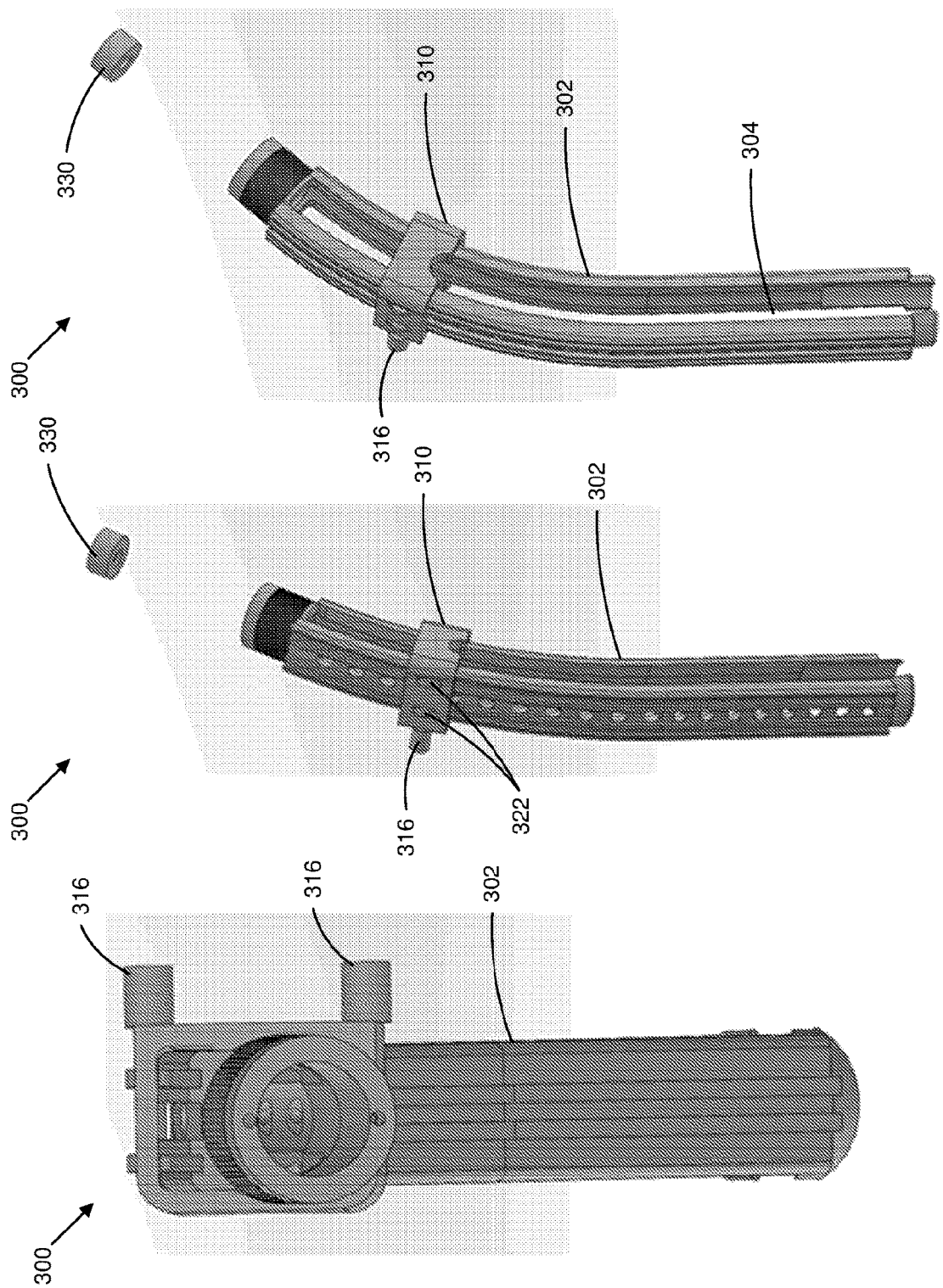

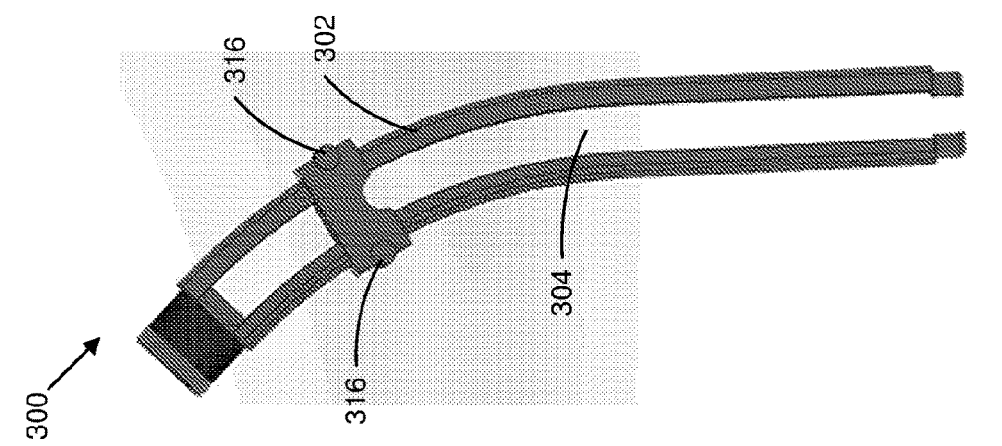
FIG. 12G
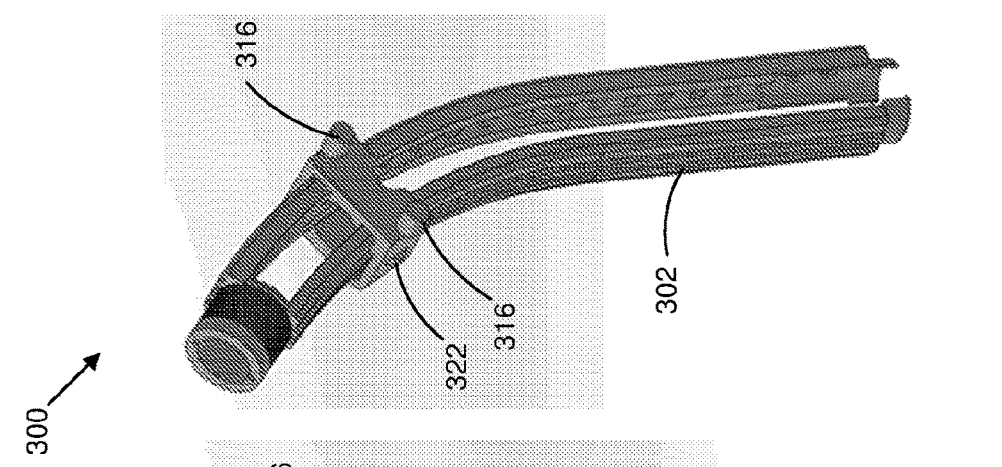
FIG. 12F
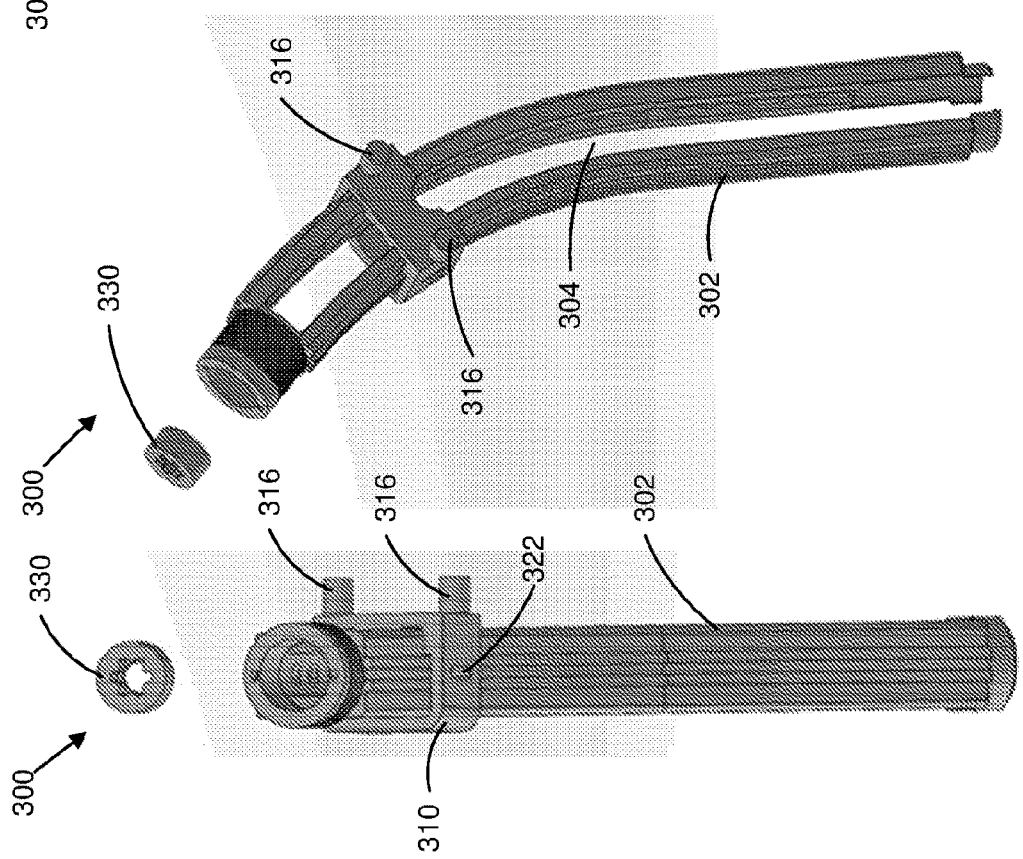
FIG. 12E
FIG. 12D

SYSTEMS, DEVICES AND METHODS FOR TREATING A LATERAL CURVATURE OF A SPINE

PRIORITY CLAIM AND INCORPORATION BY REFERENCE

The present application is a National Phase Application of PCT International Application No. PCT/US2020/062420 filed Nov. 25, 2020, titled SYSTEMS, DEVICES AND METHODS FOR TREATING A LATERAL CURVATURE OF A SPINE, which claims priority from U.S. Patent Application No. 62/941,641, filed on Nov. 27, 2019, titled SYSTEMS AND METHODS FOR CORRECTING A LATERAL CURVATURE OF A SPINE, the contents of which are hereby incorporated by reference herein in their entirety as if fully set forth herein. The benefit of priority is claimed under the appropriate legal basis including, without limitation, under 35 U.S.C. § 119 (e).

BACKGROUND

The spine or vertebral column has a natural curvature. The cervical and lumbar spine normally has a lordotic sagittal alignment whereas the thoracic spine usually has a kyphotic alignment. Variations of the typical spinal alignment curvature often occur within the "normal" range; however, "pathologic" or abnormal curvatures and alignment can occur. If the normal curvature of the spine is too excessive, then a kyphotic deformity or hyperlordosis can occur. On the other hand, if the normal curvature is reduced, then the spine is more straight and a flat back condition is seen. If the curvature is reduced even further and curves the opposite direction, then lordosis turns into kyphosis or kyphosis turns into lordosis. The reversal of normal lordosis into kyphosis is commonly seen in the cervical and sometimes lumbar spine. Sometimes pathologic conditions such as tumors, fractures, and congenital conditions such as embryological malformations and tethered cord can also cause abnormal curvature of the spine.

Lordosis and kyphosis describe the spinal alignment in the sagittal plane. In the coronal plane, abnormal curvature can also occur and is called scoliosis. Normally the spine is straight in the coronal plane. Scoliosis typically involves in thoracic and lumbar spine. In reality scoliosis is not confined to a single (coronal) plane but often involves a 3 dimensional curvature and can even include rotational curvature. Scoliosis can occur as idiopathic adolescent scoliosis that typically involves patients ages 10-18 years old. Scoliosis can also occur in adults in the form of degenerative scoliosis.

Treatment of patients with abnormalities in spinal alignment and curvature is a complex patient centered approach. Individualized treatment plans including conservative management of physical therapy, anti-inflammatory medications, and pain management is implemented first. For adolescent idiopathic scoliosis, thoraco-lumbar bracing is also employed. Surgical treatment for adolescent idiopathic scoliosis centers around correction of the clinical deformity, psychological effects of the physical deformity, and risk of progression of the deformity past skeletal maturity. Patients with idiopathic adolescent scoliosis typically do not have significant pain or altered function. In contrast, for adults with degenerative scoliosis, pain and altered function is often the prime motivation. Degenerative spine disease often presents with a mixed variety of symptoms and findings including stenosis with claudication, radiculopathy, axial back pain, disc herniation, spondylolisthesis and sagittal imbalance, lateral malalignment, and scoliosis. Thus the goals of surgery for patients with adolescent versus degenerative scoliosis can be distinct.

Techniques of surgical treatment for scoliosis typically involve restoration of alignment through spinal fusion. Both anterior instrumentation and posterior instrumentation can be used. For adolescent idiopathic scoliosis, the spine is usually flexible and so correction can be performed through pedicle screw manipulation by bending and rotation of the rod, compression and distraction of the screws on the rod, and reduction of the rod into the screw heads. When the spine is less flexible in the case of degenerative scoliosis, various forms of osteotomies, facetectomies, and interbody fusion can be performed to aid in restoration of alignment and curvature of the spine.

One of the basic techniques for restoration of scoliotic curvature is rod bending. After pedicle screws are placed, a rod is bent to fit into the screw heads of the curved spine. The rod is partially but loosely locked in by placing a screw cap or another locking device over the rod. The rod is then rotated so that the convex side of the rod is rotated posteriorly (dorsally) thereby restoring the thoracic kyphosis. In this manner the final curvature of the spine is approximately an axial rotation of the original curvature such that the convex curvature becomes the apex of the final kyphotic curve. There are also in situ benders that can bend the rod after placement into the screw heads.

There are several problems with rod bending. The main complication that can occur after scoliosis surgery is rod fracture or breakage. Although several factors contribute to rod fracture, one of the preventable factors is rod bending which weakens the metal rod and causes weakness in the rod. Rod bending increases the risk of rod breakage. (Lindsey C, Deviren V. Xu Z, et al. 2006. The effects of rod contouring on spinal construct fatigue strength. *Spine* 31: 1680-1687) (Demura et al 2015 Orthopedics 38(6):e520. Influence of rod contouring on rod strength and stiffness in spine surgery). Rod fracture has been reported as a complication of scoliosis surgery from 10-15% of patients and up to 25% in some patient populations (Buell et al 2019 J Neurosurgery Spine 21:1-14 Surgical correction of severe adult lumbar scoliosis (major curves≥75°): retrospective analysis with minimum 2-year follow-up).

Traditional techniques for reduction of spinal curvature cannot be performed without rod bending. This is because in scoliosis or deformity surgery, the spine is abnormally curved and the rod is bent to approximate the abnormal curvature in order to "fit" into the pedicle screws or extensions (also referred to herein as a towers or guiding members) connected to the pedicle screws that have been placed into the curved vertebrate. Thus the rod is bent to fit the curve.

In the ideal situation, the opposite is the goal. The vertebrate should be bent to fit the rod. Thus the abnormally curved vertebrate should be bent to conform to the idealized final shape of the rod without bending the rod. So far a method or device that can accomplish this idealized correction of spinal deformity and scoliosis has not been identified.

A "normal" cervical thoracic lumbar curvature of the spine can be generated from averaged radiographic data. However, patients come in all shapes and sizes and curvatures. In an ideal situation, deformity and scoliosis surgery would correct all spinal deformity to an idealized curvature that is directed by a pre-bent rod. In the real world, there are variations to individuals including height, age, curvature, anatomic and congenital abnormalities, severity of the deformity, osteoporosis etc. Some curves of the spine are too extreme in terms of geometry or degree of flexibility to correct completely because the forces required to make the full correction may cause fracture of the vertebrate, pedicles, lamina, etc., or risk neurological injury due to abnormal movement and shifting during the correction. Computational models have been developed that can predict an optimal 3 dimensional shape of the rod for each individualized (Kokabu et al 2018 J.Orthop.Res 36:3219-3224 Identification of optimized rod shapes to guide anatomical spinal reconstruction for adolescent thoracic idiopathic scoliosis). Other methods have utilized artificial intelligence (AI) and machine learning to optimize rod shaping prior to surgery.

SUMMARY OF SOME EMBODIMENTS

Disclosed herein are embodiments of systems, devices and methods for correcting a lateral curvature of a spine. Hereinafter, systems, devices and methods for correcting a lateral curvature of a spine may also be referred to as systems, devices and methods and/or systems, devices and methods for treating spinal defects.

Some embodiments of the systems, devices and methods can include a plurality of screws configured to be implanted in a plurality of vertebrae, and a plurality of extensions (which may also be referred to herein as guiding members) configured to be removably coupled with the plurality of screws. The plurality of extensions can be curved along at least a portion thereof and can be removably coupled with a screw head of each of the plurality of screws. In some embodiments, one or more of the extensions can be curved along all or substantially all of a length of the extension. Further, the systems, devices and methods can include a connecting element or rod that is configured to be coupled with the plurality of screw heads. Some embodiments can be configured such that the rod can be guided along the plurality of extensions (for example and without limitation, along a channel extending along a length of the extensions) from the proximal toward the distal ends of the extensions and into engagement with the plurality of screws to cause the plurality of vertebrae to move laterally.

Some embodiments of the systems, devices and methods disclosed herein for treating a lateral curvature of a spine can include a plurality of screws configured to be implanted in a plurality of vertebrae, each of the plurality of screws having a screw head, a plurality of extensions configured to be removably coupled with the plurality of screws, each of the plurality of extensions having a proximal end portion, a distal end portion configured to be removably coupled with the screw head of each of the plurality of screws, and a middle portion between the proximal end portion and the distal end portion, and a rod that is configured to be coupled with the plurality of screw heads.

Any embodiments of the systems, devices, and/or methods disclosed herein can include, in additional embodiments, one or more of the following features, components, and/or details, in any combination with any of the other features, components, and/or details of any other embodiments disclosed herein: wherein an axial centerline of the proximal end portion of at least one of the extensions can be at a different angle than an axial centerline of the distal end portion of the at least one of the extensions; wherein the device can be configured such that the rod can be guided along the plurality of extensions from the proximal ends of the plurality of extensions toward the distal end portions of the plurality of extensions and into engagement with the plurality of screws; wherein at least the middle portion of the plurality of extensions are curved; wherein at least the middle portion of the plurality of extensions are bent; wherein the angle of the axial centerline of the proximal end portion relative to the axial centerline of the distal end portion of at least one of the extensions is adjustable by a surgeon during a procedure to treat a lateral curvature of the spine; wherein at least one of the extensions can be locked in a desired angular position after the angle of the axial centerline of the proximal end portion relative to the axial centerline of the distal end portion of at least one of the extensions is adjusted; wherein the angle of the axial centerline of the proximal end portion relative to the axial centerline of the distal end portion of at least one of the extensions is adjustable by a robot during a procedure to treat a lateral curvature of the spine; wherein an axial centerline of the proximal end portion of at least two of the extensions is at a different angle than an axial centerline of the distal end portion of the at least two of the extensions; wherein the device can include a first extension, wherein an axial centerline of the proximal end portion of first extension is at a first angle relative to an axial centerline of the distal end portion of the first extension, wherein the first angle is greater than zero; wherein the device can include a second extension, wherein an axial centerline of the proximal end portion of second extension is at a second angle relative to an axial centerline of the distal end portion of the second extension, wherein the second angle is greater than the first angle; wherein the device can include a third extension, wherein an axial centerline of the proximal end portion of third extension is at a third angle relative to an axial centerline of the distal end portion of the third extension, wherein the third angle is greater than the second angle; wherein the device can include a fourth extension and a fifth extension, wherein an axial centerline of the proximal end portion of fourth extension is at a fourth angle relative to an axial centerline of the distal end portion of the fourth extension, the fourth angle is greater than the third angle, an axial centerline of the proximal end portion of fifth extension is at a fifth angle relative to an axial centerline of the distal end portion of the fifth extension, and the fifth angle is greater than the fourth angle; wherein the device can include a sixth extension, wherein an axial centerline of the proximal end portion of sixth extension is collinear with an axial centerline of the distal end portion of the sixth extension; wherein the device is configured to move one or more vertebra in a lateral direction as the rod is advanced toward the distal end portions of the plurality of extensions and into engagement with the plurality screw heads; wherein the device is configured to move one or more vertebra toward a lateral centerline of the spine as the rod is advanced toward the distal end portions of the plurality of extensions; wherein the device is configured such that the rod can be simultaneously advanced down the plurality of extensions by incrementally advancing the rod toward the distal end portion of each of the plurality of extensions; wherein the rod is generally straight in at least a lateral direction; and/or wherein the plurality of extensions have varying lengths; and/or wherein the plurality of extensions have varying curvatures such that a curvature of a first of the plurality of extensions is different than a curvature of a second of the plurality of extensions.

Further, any embodiments of the systems, devices, and/or methods disclosed herein can include, in additional embodiments, one or more of the following features, components, and/or details, in any combination with any of the other features, components, and/or details of any other embodiments disclosed herein: wherein each of the plurality of extensions has a slot therein extending from the proximal end portion toward the distal end portion of each of the plurality of extensions, wherein the slot of each of the plurality of extensions is configured to slidably receive the rod therein such that the rod can be guided toward the plurality of screw heads through the slots of the plurality of extensions; wherein the device can include a plurality of push elements configured to be advanced along the slot between the proximal and distal end portions of each of the plurality of extensions; wherein the slot of each of the plurality of extensions has internal threads therein configured to threadedly engage with a plurality of threaded push elements that can be threadedly advanced in the slots toward the distal end portions of the plurality of extensions to cause the rod to be advanced toward the plurality of screw heads; wherein the device can include a plurality of push elements configured to couple with the plurality of extensions and to selectively move the rod down toward the distal end portions of the plurality of extensions toward the plurality of screw heads as the plurality of push elements are advanced toward the distal end portions of the plurality of extensions; wherein the plurality of push elements are each selectively biased against moving toward the proximal end portions of the plurality of extensions as the plurality of push elements are advanced toward the distal end portions of the plurality of extensions; wherein the device can include a plurality of threaded screws configured to threadedly engage with the plurality of extensions and to selectively move the rod down toward the distal end portions of the plurality of extensions toward the plurality of screw heads as the plurality of screws are threadedly advanced toward the distal end portions of the plurality of extensions; wherein the device is configured to inhibit the rod from moving toward the proximal end portion of each of the plurality of extensions as the rod is being advanced toward the distal end portion of each of the plurality of extensions; wherein the device can include a plurality of guide elements configured to couple with the rod and to slide along the plurality of extensions from the proximal end portion of each of the plurality of extensions toward the distal end portion of each of the plurality of extensions to guide the rod toward the plurality of screw heads; and/or wherein at least one of the plurality of extensions is approximately straight portion along a length of extension.

Further, any embodiments of the systems, devices, and/or methods disclosed herein can include, in additional embodiments, one or more of the following features, components, and/or details, in any combination with any of the other features, components, and/or details of any other embodiments disclosed herein: wherein the plurality of screws comprises a first plurality of screws and a second plurality of screws, the device is configured such that the first plurality of screws will each be implanted in a plurality of vertebrae adjacent (for example, bilaterally adjacent) to each of the second plurality of screws, the plurality of extensions comprises a first plurality of extensions and a second plurality of extensions, each of the first plurality of extensions is configured to be removably coupled with the screw head of each of the first plurality of screw heads, each of the second plurality of extensions is configured to be removably coupled with the screw head of each of the second plurality of screw heads, the rod is a first rod and the device comprises a second rod, and the device is configured such that the first rod is guidable along the first plurality of extensions from the proximal end portions of the first plurality of extensions toward the distal end portions of the first plurality of extensions and into engagement with the first plurality of screws, and such that the second rod is guidable along the second plurality of extensions from the proximal end portions of the second plurality of extensions toward the distal end portions of the second plurality of extensions and into engagement with the second plurality of screws; wherein the device can include a first screw having a first screw head, a second screw having a second screw head, a third screw having a third screw head, a first extension having a proximal end portion, a distal end portion configured to be removably couplable with the first screw head, and a body portion between the proximal and distal end portions, wherein at least a portion of the first extension is curved, a second extension having a proximal end portion, a distal end portion configured to be removably couplable with the second screw head, and a body portion between the proximal and distal end portions, wherein at least a portion of the second extension is curved, and a third extension having a proximal end portion, a distal end portion configured to be removably couplable with the third screw head, and a body portion between the proximal and distal end portions, wherein at least a portion of the third extension is curved; wherein the body portion of the first extension has a first curvature, the body portion of the second extension has a second curvature, and the second curvature is different than the first curvature; wherein the body portion of the second extension has a second curvature, the body portion of the third extension has a third curvature, and the third curvature is different than the second curvature; wherein the plurality of extensions has at least four different curvatures and/or lengths; wherein the device can include a plurality of locking caps each configured to engage with the screw head of each of the plurality of screws; and/or wherein the device can include a plurality of torque or pressure sensors, wherein each of the torque or pressure sensors are coupled with the plurality of extensions and are configured to operably measure an amount of strain at a plurality of the extensions.

Also disclosed herein are embodiments of systems and devices for treating device for treating a lateral curvature of a spine, that can include a plurality of screws configured to be implanted in a plurality of vertebrae having a plurality of screw heads, and a plurality of extensions configured to be removably coupled with the plurality of screws, each of the plurality of extensions having a proximal end portion, a distal end portion configured to be removably coupled with the screw head of each of the plurality of screws, and a middle portion between the proximal end portion and the distal end portion.

Any embodiments of the devices, systems, and/or methods disclosed herein can include, in additional embodiments, one or more of the following features, components, and/or details, in any combination with any of the other features, components, and/or details of any other embodiments disclosed herein: wherein a proximal end portion of a first extension of the plurality of extensions is laterally spaced apart or offset from a distal end portion of the first extension by a first distance when the first extension is coupled with a first vertebra in an operable position, a proximal end portion of a second extension of the plurality of extensions is laterally spaced apart from a distal end portion of the second extension by a second distance when the second extension is coupled with a second vertebra in an operable position, and the second distance is greater than the first distance; wherein at least one of the first distance of the first extension and the second distance of the second extension are adjustable by a surgeon during a procedure to treat a lateral curvature of the spine; wherein at least one of the first distance of the first extension and the second distance of the second extension are adjustable by a robot during a procedure to treat a lateral curvature of the spine; wherein a proximal end portion of a third extension of the plurality of extensions is laterally spaced apart from a distal end portion of the third extension by a third distance when the third extension is coupled with a third vertebra in an operable position, and the third distance is greater than the second distance; wherein a proximal end portion of a fourth extension of the plurality of extensions is laterally spaced apart from a distal end portion of the fourth extension by a fourth distance when the fourth extension is coupled with a fourth vertebra in an operable position, a proximal end portion of a fifth extension of the plurality of extensions is laterally spaced apart from a distal end portion of the fifth extension by a fifth distance when the fifth extension is coupled with a fifth vertebra in an operable position, the fourth distance is greater than the third distance, and the fifth distance is greater than the fourth distance; wherein at least the middle portion of the plurality of extensions are curved, bent, and/or angled; and/or wherein the plurality of extensions comprises a generally straight extension.

Further, in any embodiments disclosed herein, a distal end portion of at least one of the plurality of extensions can be flexibly coupled with the corresponding screw and/or screw head in any embodiments disclosed herein. For example and without limitation, the system can be configured such that at least one of the plurality of extensions is (or, in other embodiments, all of the plurality of extensions are) configured to rotate in a lateral direction (or at least in a lateral direction) relative to a corresponding screw that the extension is coupled with, wherein the lateral direction is the direction in a plane that is perpendicular to a centerline of the spine. For example and without limitation, the extension can be configured to rotate relative to an axial centerline of a corresponding screw within a range of 20 degrees or approximately 20 degrees, or within a range of 10 degrees or approximately 10 degrees, in a lateral direction, wherein the lateral direction is the direction in a plane that is perpendicular to a centerline of the spine. In any embodiments, the system can be configured wherein the distal end portion of each of the plurality of extensions is configured to be rigidly coupled with a corresponding one of the plurality of screws and/or a corresponding one of the plurality of screw heads such that at least the distal end portion of each of the plurality of extensions is axially aligned with the corresponding screw and/or screw head and is inhibited from rotating relative to each of the plurality of screws in an operable position.

Further, any embodiments of the devices, systems, and/or methods disclosed herein can include, in additional embodiments, one or more of the following features, components, and/or details, in any combination with any of the other features, components, and/or details of any other embodiments disclosed herein: wherein the device can include a rod that is configured to be coupled with the plurality of screw heads, wherein the device is configured to move one or more vertebra in a lateral direction as the rod is advanced toward the distal end portions of the plurality of extensions and into engagement with the plurality screw heads; wherein the device is configured such that the rod can be simultaneously advanced down the plurality of extensions by incrementally advancing the rod toward the distal end portion of each of the plurality of extensions; wherein the rod is generally straight in at least a lateral direction; wherein the plurality of extensions have varying lengths; wherein each of the plurality of extensions has a slot therein extending from the proximal end portion toward the distal end portion of each of the plurality of extensions, wherein the slot of each of the plurality of extensions is configured to slidably receive the rod therein such that the rod can be guided toward the plurality of screw heads through the slots of the plurality of extensions; wherein the device can include a plurality of push elements configured to be advanced along the slot between the proximal and distal end portions of each of the plurality of extensions; wherein the device can include a plurality of push elements configured to couple with the plurality of extensions and to selectively move the rod down toward the distal end portions of the plurality of extensions toward the plurality of screw heads as the plurality of push elements are advanced toward the distal end portions of the plurality of extensions; and/or wherein the device can include a plurality of threaded screws configured to threadedly engage with the plurality of extensions and to selectively move the rod down toward the distal end portions of the plurality of extensions toward the plurality of screw heads as the plurality of screws are threadedly advanced toward the distal end portions of the plurality of extensions.

Some embodiments of the systems, devices and methods disclosed herein for treating a lateral curvature of a spine can include a plurality of screws configured to be implanted in a plurality of vertebrae, each of the plurality of screws having a screw head, a plurality of curved or bent extensions configured to be removably coupled with the plurality of screws, each of the plurality of curved or bent extensions having a proximal end, a distal end configured to be removably coupled with the screw head of each of the plurality of screws, and a body portion between the proximal end and the distal end, wherein the plurality of extensions are curved or bent along at least a portion thereof, and a rod that is configured to be coupled with the plurality of screw heads.

Any embodiments of the devices, systems, and/or methods disclosed herein can include, in additional embodiments, one or more of the following features, components, and/or details, in any combination with any of the other features, components, and/or details of any other embodiments disclosed herein: wherein the system can be configured such that the rod can be guided along the plurality of curved or bent extensions from the proximal ends of the plurality of curved or bent extensions toward the distal ends of the plurality of curved or bent extensions and into engagement with the plurality of screws; wherein the system can be configured to move one or more vertebra in a lateral direction as the rod is advanced toward the distal ends of the plurality of curved or bent extensions and into engagement with the plurality screw heads; wherein the system can be configured such that the rod can be simultaneously advanced down the plurality of curved or bent extensions by incrementally advancing the rod toward the distal end of each of the plurality of curved or bent extensions; wherein the system can be configured to move one or more vertebra toward a lateral centerline of the spine as the rod is advanced toward the distal ends of the plurality of curved or bent extensions; wherein the rod can be generally straight in the lateral direction; wherein the plurality of curved or bent extensions can have varying lengths; wherein the plurality of curved or bent extensions can have varying curvatures; and/or wherein each of the plurality of curved or bent extensions can have a slot therein extending from the proximal end of each of the plurality of curved or bent extensions toward the distal end of each of the plurality of curved or bent extensions, wherein the slot of each of the plurality of curved or bent extensions can be configured to slidably receive the rod therein such that the rod can be guided toward the plurality of screw heads using the slots of the plurality of curved or bent extensions.

Further, any embodiments of the systems, devices, and/or methods disclosed herein can include, in additional embodiments, one or more of the following features, components, and/or details, in any combination with any of the other features, components, and/or details of any other embodiments disclosed herein: including a plurality of push elements configured to couple with the plurality of curved or bent extensions and to selectively move the rod down toward the distal ends of the plurality of curved or bent extensions toward the plurality of screw heads as the plurality of push elements are advanced toward the distal ends of the plurality of curved or bent extensions; wherein the plurality of push elements are each selectively biased against moving toward the proximal end of the plurality of curved or bent extensions as the plurality of push elements are advanced toward the distal ends of the plurality of curved or bent extensions; further including a plurality of threaded push elements configured to threadedly engage with the plurality of curved or bent extensions and to selectively move the rod down toward the distal ends of the plurality of curved or bent extensions toward the plurality of screw heads as the plurality of push elements are threadedly advanced toward the distal ends of the plurality of curved or bent extensions; wherein the plurality of threaded push elements can be a plurality of screws; wherein each of the plurality of curved or bent extensions can have a slot therein extending from the proximal end of each of the plurality of curved or bent extensions toward the distal end of each of the plurality of curved or bent extensions, wherein the slot of each of the plurality of curved or bent extensions can be configured to slidably receive the rod therein such that the rod can be guided toward the plurality of screw heads using the slots of the plurality of curved or bent extensions; further including a plurality of push elements configured to engage with the slot of each of the plurality of extensions; wherein the slot of each of the plurality of curved or bent extensions has internal threads therein configured to threadedly engage with a plurality of threaded push elements that can be threadedly advanced in the slots toward the distal ends of the plurality of curved or bent extensions to cause the rod to be advanced toward the plurality of screw heads; wherein the system can be configured to selectively prevent the rod from moving toward the proximal end of each of the plurality of curved or bent extensions as the rod is being advanced toward the distal end of each of the plurality of curved or bent extensions; further including a plurality of guide elements configured to couple with the rod and to slide along the plurality of curved or bent extensions from the proximal end of each of the plurality of curved or bent extensions toward the distal end of each of the plurality of curved or bent extensions to guide the rod toward the plurality of screw heads; and/or wherein at least one of the plurality of curved or bent extensions has at least one approximately straight portion along a length of curved or bent extension.

Further, any embodiments of the systems, devices, and/or methods disclosed herein can include, in additional embodiments, one or more of the following features, components, and/or details, in any combination with any of the other features, components, and/or details of any other embodiments disclosed herein: wherein the plurality of screws can include a first plurality of screws and a second plurality of screws, the system can be configured such that the first plurality of screws will each be implanted in a plurality of vertebrae adjacent to each of the second plurality of screws, the plurality of curved or bent extensions can include a first plurality of curved or bent extensions and a second plurality of curved or bent extensions, each of the first plurality of curved or bent extensions can be configured to be removably coupled with the screw head of each of the first plurality of screw heads; each of the second plurality of curved or bent extensions can be configured to be removably coupled with the screw head of each of the second plurality of screw heads, the rod is a first rod and the system can include a second rod, and the system can be configured such that the first rod is guidable along the first plurality of curved or bent extensions from the proximal ends of the first plurality of curved or bent extensions toward the distal ends of the first plurality of curved or bent extensions and into engagement with the first plurality of screws, and such that the second rod is guidable along the second plurality of curved or bent extensions from the proximal ends of the second plurality of curved or bent extensions toward the distal ends of the second plurality of curved or bent extensions and into engagement with the second plurality of screws; further including a first screw having a first screw head, a second screw having a second screw head, a third screw having a third screw head, a first extension having a proximal end, a distal end configured to be removably couplable with the first screw head, and a body portion between the proximal and distal ends, wherein at least a portion of the first extension is curved or bent, a second extension having a proximal end, a distal end configured to be removably couplable with the second screw head, and a body portion between the proximal and distal ends, wherein at least a portion of the second extension is curved or bent, and a third extension having a proximal end, a distal end configured to be removably couplable with the third screw head, and a body portion between the proximal and distal ends, wherein at least a portion of the third extension is curved or bent, wherein the body portion of the first extension has a first curvature, the body portion of the second extension has a second curvature, and the second curvature is different than the first curvature; wherein the body portion of the second extension has a second curvature, the body portion of the third extension has a third curvature, and the third curvature is different than the second curvature; wherein the plurality of curved or bent extensions has at least four different curvatures and/or lengths; and/or further including a plurality of locking caps each configured to engage with the screw head of each of the plurality of screws.

Some embodiments of the systems, devices and methods disclosed herein for treating a lateral curvature of a spine can include a plurality of rod lowering devices configured to assist with a lowering of a rod into the plurality of screw heads, each rod lowering device including a body portion having a passageway, the passageway being configured to receive a corresponding one of a plurality of extensions therein as the rod lowering devices are passed over the plurality of extensions, and a contact member configured to translate along a length of the body portion of each of the rod lowering devices and to removably couple with the rod that can be configured to be coupled with the plurality of screw heads.

Any embodiments of the systems, devices, and/or methods disclosed herein can include, in additional embodiments, one or more of the following features, components, and/or details, in any combination with any of the other features, components, and/or details of any other embodiments disclosed herein: wherein each of the body portions have a distal end portion configured to be removably coupled with a corresponding one of a screw, a corresponding one of a screw head, and/or a distal portion of a corresponding one of an extension; wherein the rod lowering devices are configured to move the rod toward the screw heads as the contact members are moved toward the screw heads; wherein the body portion of one or more of the rod lowering devices has one or more grooves along the length thereof, wherein the grooves are each configured to receive a portion of the contact member therein as the contact member is advanced along the length of the body portion of the respective rod lowering device; wherein the body portion of one or more of the rod lowering devices has one or more grooves along the length thereof, wherein the grooves are each configured to receive a projection or a wheel of the contact member therein as the contact member is advanced along the length of the body portion of the respective rod lowering device; wherein the rod lowering devices are all straight; wherein the rod lowering devices are all curved; wherein the contact member can be configured to roll or slide relative to the body portion; wherein the passageway is threaded; further including a threaded cap configured to be threadedly advanced down the passageway toward the screw head, and configured to threadedly couple with each of the plurality of screw heads to secure the rod to the plurality of screw heads; further including a force sensor coupled with the rod lowering device configured to measure a level of force being applied to the rod; and/or further including a torque sensor configured to measure a level of torque being applied to the cap.

Some embodiments of the systems, devices and methods disclosed herein for treating a lateral curvature of a spine can include a plurality of screws each configured to be implanted in a corresponding one of a plurality of vertebrae, each of the plurality of screws having a screw head, and a plurality of extensions each configured to be removably coupled with a corresponding one of the plurality of screws, each of the plurality of extensions having first guide configured to be coupled with a first side of the screw head and a second guide configured to be coupled with a second side of the screw head, the second side being opposite the first side, and wherein the first guide and the second guide diverge laterally outwardly away from a centerline axis of the device such that a width between a proximal end portions of the first guide and the second guide is greater than a width between a distal end portion of the first guide and the second guide.

Any embodiments of the systems, devices, and/or methods disclosed herein can include, in additional embodiments, one or more of the following features, components, and/or details, in any combination with any of the other features, components, and/or details of any other embodiments disclosed herein: wherein the width between the proximal end portions of the first guide and the second guide can be adjusted by a surgeon during a procedure to treat a lateral curvature of the spine; wherein the width between the proximal end portions of the first guide and the second guide can be adjusted by a robot during a procedure to treat a lateral curvature of the spine; further including a first extension and a second extension, wherein a width between proximal end portions of a first guide and a second guide of the first extension is less than a width between proximal end portions of a first guide and a second guide of the second extension; further including a third extension, wherein the width between the proximal end portions of the first guide and the second guide of the second extension is less than a width between proximal end portions of a first guide and a second guide of the third extension; further including a fourth extension, wherein the width between the proximal end portions of the first guide and the second guide of the third extension is less than a width between proximal end portions of a first guide and a second guide of the fourth extension; further including a fifth extension, wherein the width between the proximal end portions of the first guide and the second guide of the fourth extension is less than a width between proximal end portions of a first guide and a second guide of the fifth extension; further including a sixth extension, wherein the width between the proximal end portions of the first guide and the second guide of the fifth extension is less than a width between proximal end portions of a first guide and a second guide of the sixth extension; wherein at least a portion of the first and second guides are curved, bent, and/or angled; wherein the plurality of extensions can include a generally straight extension; and/or further including a rod that can be configured to be coupled with the plurality of screw heads, wherein the system can be configured to move one or more vertebra in a lateral direction as the rod is advanced toward the distal end portions of the plurality of extensions and into engagement with the plurality screw heads.

Some embodiments of the systems, devices and methods disclosed herein for treating a lateral curvature of a spine can include a plurality of screws each configured to be implanted in a corresponding one of a plurality of vertebrae, each of the plurality of screws having a screw head, a plurality of extensions each configured to be removably coupled with a corresponding one of the plurality of screws and/or screw heads at a distal end portion thereof, a plurality of guiding members configured to be coupled with a proximal end portion of each of the plurality of extensions, and an alignment element configured to be advanced over the plurality of guiding members, wherein the system is configured to move one or more vertebra toward a lateral centerline of the spine as the alignment element is advanced toward the distal end portions of the plurality of guiding members.

Any embodiments of the systems, devices, and/or methods disclosed herein can include, in additional embodiments, one or more of the following features, components, and/or details, in any combination with any of the other features, components, and/or details of any other embodiments disclosed herein: a proximal end portion of a first guiding member of the plurality of guiding members is laterally spaced apart from a distal end portion of the first guiding member by a first distance when the first guiding member is coupled with a first extension of the plurality of extensions in an operable position; wherein a proximal end portion of a second guiding member of the plurality of guiding members is laterally spaced apart from a distal end portion of the second guiding member by a second distance when the second guiding member is coupled with a second extension of the plurality of extensions in an operable position, and wherein the second distance is greater than the first distance; wherein at least one of the first distance of the first guiding member and the second distance of the second guiding member is adjustable by a surgeon during a procedure to treat a lateral curvature of the spine; wherein at least one of the first distance of the first guiding member and the second distance of the second guiding member is adjustable by a robot during a procedure to treat a lateral curvature of the spine; wherein a proximal end portion of a third guiding member of the plurality of guiding members is laterally spaced apart from a distal end portion of the third guiding member by a third distance when the third guiding member is coupled with a third extension in an operable position, and the third distance is greater than the second distance; wherein a proximal end portion of a fourth guiding member of the plurality of guiding members is laterally spaced apart from a distal end portion of the fourth guiding member by a fourth distance when the fourth guiding member is coupled with a fourth extension in an operable position and the fourth distance is greater than the third distance; wherein a proximal end portion of a fifth guiding member of the plurality of guiding members is laterally spaced apart from a distal end portion of the fifth guiding member by a fifth distance when the fifth guiding member is coupled with a fifth extension in an operable position, and the fifth distance is greater than the fourth distance; wherein the system is configured such that the plurality of guiding members are positioned completely outside a body of a patient in an operable position; wherein the system is configured such that the alignment element is positioned completely outside a body of a patient when the alignment element is in an operable position adjacent to the distal end portion of the plurality of guiding members; and/or wherein the plurality of guiding members comprise guiding members that are curved, bent, and/or angled; wherein the plurality of guiding members are curved; wherein the plurality of guiding members comprises at least one generally straight guiding member.

Further, any embodiments of the systems, devices, and/or methods disclosed herein can include, in additional embodiments, one or more of the following features, components, and/or details, in any combination with any of the other features, components, and/or details of any other embodiments disclosed herein: further including a rod that is configured to be coupled with the plurality of screw heads to inhibit the one or more vertebra from moving away from the lateral centerline of the spine; wherein the rod is generally straight in at least a lateral direction; wherein each of the plurality of extensions has a slot therein extending from the proximal end portion toward the distal end portion of each of the plurality of extensions, wherein the slot of each of the plurality of extensions is configured to slidably receive the rod therein such that the rod can be guided toward the plurality of screw heads through the slots of the plurality of extensions; further including a plurality of caps configured to be advanced through each of the plurality of extensions to move the rod toward the plurality of screw heads; and/or wherein a distal end portion of each of the plurality of guiding members are coupled with the proximal end of the plurality of extensions at a position that is laterally offset from an axial centerline of the plurality of extensions.

Some embodiments of the systems, devices and methods disclosed herein for treating a lateral curvature of a spine can include a plurality of screws configured to be implanted in a plurality of vertebrae, each of the plurality of screws having a screw head, a plurality of curved or bent guiding elements each configured to be fixed relative to a corresponding screw, each of the plurality of curved or bent guiding elements having a proximal end and a distal end, and a rod that is configured to be guided along the plurality of curved or bent guiding elements from the proximal ends of the plurality of curved or bent guiding elements toward the distal ends of the plurality of curved or bent guiding elements, wherein the system is configured such that guiding of the rod along the plurality of curved or bent guiding elements causes the plurality of vertebrae to move to correct the lateral curvature of the spine.

Any embodiments of the systems, devices, and/or methods disclosed herein can include, in additional embodiments, one or more of the following features, components, and/or details, in any combination with any of the other features, components, and/or details of any other embodiments disclosed herein: the distal ends of the plurality of curved or bent guiding elements are each configured to be fixed relative to the screw head of a corresponding screw, and the rod is configured to be guided by the plurality of curved or bent guiding elements into the screw heads of the plurality of screws; a plurality of towers each having a proximal end and a distal end, wherein the distal ends of the plurality of towers are each configured to be fixed relative to the screw head of a corresponding screw, and the distal ends of the plurality of curved or bent guiding elements are each configured to be fixed to the proximal ends of a corresponding tower; the plurality of towers each comprise an opening or slot configured to guide a spinal fixation rod into the screw heads of the plurality of screws; further comprising a spinal fixation rod, wherein the spinal fixation rod is separate from the rod configured to be guided along the plurality of curved or bent guiding elements; wherein the plurality of towers each further comprise a preloaded cap at the proximal end of each tower.

BRIEF DESCRIPTION OF THE DRAWINGS

The accompanying drawings, which are incorporated in and constitute a part of the specification, illustrate embodiments of the disclosure, and together with the general description given above and the detailed description of the embodiments given below, serve to explain the principles of the embodiments of the disclosure.

FIGS. 12A-12G show another embodiment of a rod lowering device that can be used with any of the systems or devices disclosed herein for treating the spine.

DETAILED DESCRIPTION OF SOME EMBODIMENTS

Figure 1:
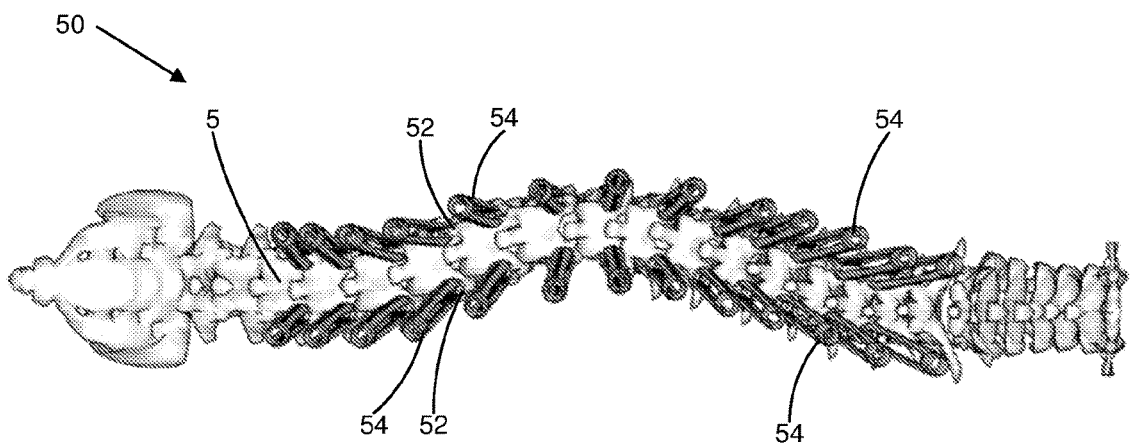
FIG. 1 is a top view of a spine having lateral curvature defects, and having a plurality of pedicle screws implanted in the spine.

Some embodiments of the devices and methods disclosed herein start with an optimized pre-shaped rod and bends the spine to fit the rod instead of bending the rod to fit the spine during spinal deformity and scoliosis surgery.

In some embodiments, a system or plurality of bent or curved towers and blades that are attached to pedicle screws can guide a pre-bent rod into the seat of the pedicle screw head during spinal deformity and scoliosis surgery. Traditional towers and reduction constructs used to reduce a rod into the seat of the head of the pedicle screw are straight. The straight towers or reduction constructs can be angled in different directions if the head of the pedicle screw is polyaxial. However in deformity correction surgery, polyaxial screws reduce the ability to reduce the spinal deformity because any correction made by imposing forces at the tower or rod (rod rotation, reduction, etc.), causes the polyaxial pedicle screw head to rotate in its polyaxial joint rather than rotate the actual vertebrate. The purpose of the polyaxial screw head is to compensate for variations of screw to rod alignment, otherwise the rod would have to be perfectly aligned and angled within the screw head.

By using customized curved or bent towers or blades, a pre-bent rod with a fixed optimized final shape can be fitted within the system of bent or curved towers and slowly lowered into the seat of the screws. In this manner the heads of the pedicle screws do not have to be polyaxial. The screws can be fixed angle screws where the screw heads cannot move in relation to the threaded shaft of the screw. Alternatively, the screw head can be uniaxial (monaxial) or have a limited polyaxial rotation. By limiting the degrees of movement and rotation between the screw head and the screw shaft, rotation and reduction of the rod into the vertebrate will cause rotation and reduction of the vertebral body instead of the head of the polyaxial screw.

In another preferred embodiment, the blades or walls of the towers are divergent from the distal end connected to the screw head towards the proximal end outside the body. The divergent spread of the blades or walls of the towers allow easier "capture" of the pre-bent rod. Essentially this opening of the blades or tower at the proximal end allows an entry zone for the pre-bent rod to be easily inserted through the towers of all the screws. The mechanism by which the rod is lowered down the tower to the distal end in this case then needs to accommodate this proximal divergence. For example, a simple cap screwing down a threaded track within a curved or bent tower is no longer sufficient if the walls of the tower is too wide for a cap to touch both sides. Instead an external track located on the sides or outside of the wall of the tower and a gear system that allows a pusher to travel down the tower using the track and gear system then allows the rod pusher to run on just one wall instead of having to contact both walls.

In some embodiments, the system of curved or bent towers can allow a smooth transition from the initial pathologic spinal curve to the idealized final curvature allowing the pre-bent optimized rod to be lowered into the screw heads. A traditional technique using straight towers requires correction of the deformity sequentially (Buchholz et al 2020 Operative Neurosurgery19(2):E157-E158 Deformity correction through the use of reduction towers: 2-dimensional operative video. https://academic.oup.com/ons/article/19/2/E157/5673648). When using traditional straight towers, the rod is captured into each pedicle screw sequentially, one at a time. Also only one side (rod) is placed at a time. In some embodiments of the device and/or method for treating lateral curvature of the spine disclosed herein, towers (that can be curved or bent) are designed to bring the pre-bent rod into the seat of all the pedicle screws simultaneously. Both left and right rods can be lowered at the same time without interference. By lowering both rods simultaneously, the load of the strain of the correction of the deformity is shared between the pedicle screws on both sides, thus reducing the risk of pedicle fracture and screw loosening. Similarly by lowering the rod simultaneously using all towers and all screws simultaneously, the correction of the deformity is shared amongst all screws as compared with a sequential approach as shown in the video using straight towers.

In the case using straight towers, each screw is "captured" sequentially, and in this manner, the most force or strain is placed at the site between the last screw captured and the next screw to be captured in the sequence. This concept is commonly seen in spinal fusion surgery as the adjacent level phenomenon. It is the level adjacent to the fusion that experiences the most strain and thus has highest risk for further degeneration. Thus once the rod has been placed into the towers and screw heads of some screws, these screws are essentially constrained or partially fused, i.e. they move together and their movements are constrained. Thus in capturing the next pedicle screw in a sequential manner will cause momentary increase in strain at the level of the next level in the sequence. On the other hand by lowering the rod simultaneously, all the screws can experience similar strain. This is essentially load sharing and allows the strain of the correction of the deformity to be shared broadly amongst all the pedicle screws.

Any embodiments disclosed herein can include torque or pressure sensors. Such torque or pressure sensors can be positioned at the site of rod lowering within each extension or tower. Further, a rod lowering device within each extension of any embodiments of the devices for treating a lateral curvature of the spine disclosed herein can be coordinated such that the torque or load of rod lowering is shared amongst all the extensions.

By using a coordinated lowering of the rod within all the extensions (which can be curved), the rod is lowered in the safest and most predictable manner Both sides can be performed simultaneously. Additionally, coordination and automated application of torque or pressure at each tower is a robotic process. Instead of the traditional robot arm used in spine surgery, this robotic device can monitor the strain that is experienced at the rod within each of the curved towers simultaneously. In some embodiments, the rod within towers experiencing lower strain is preferentially lowered relative to the rod within towers experiencing higher strain. This way the rod is lowered into the heads of the screw and the spinal deformity is corrected more evenly in some embodiments, in terms of strain on the vertebral segments. If the strain as measured by a torque or strain sensor or transducer exceeds a cutoff, then a feedback system stops the entire system to prevent the risk of vertebral or pedicle breakage. Furthermore if there is a sudden change in the torque or strain such as sudden drop, then this may indicate a pedicle fracture or screw fracture or pullout. Thus this sudden change including drop in strain would indicate the need to stop.

During the rod lowering process, in some embodiments, the spinal deformity correction can be assisted by rotation of the rod or manipulation of the surgical bed, or application of forces external to the body. Rod rotation has been the mainstay of traditional deformity correction. Controlled rod rotation using a robotic mechanism is also helpful with some embodiments of the methods and devices disclosed herein, in addition to optimizing the curvature of the bent towers. Additionally, chiropractors and physical therapists often use external braces and chairs including external bracing to reduce scoliotic deformity. Such external forces can be applied during surgery to assist in deformity correction as well. External forces can be applied using inflatable air bags located at the sides of the body as well as gears located inside the bed that allow the operative bed to bend. The ProAxis by Mizuho OSI operative bed is one example of a bed that can adjust the exact degree of flexion and extension with the touch of a button. Using a unified approach using both external forces and internal forces will help correct the deformity during surgery safely and quickly.

Newer techniques used in scoliosis surgery, particularly in adolescent idiopathic scoliosis and early onset scoliosis have used growing rod techniques and even magnetically controlled growing rods. Some of these rod devices have internal gears and machinery. Others have used multiple rods and larger rods to reduce the risk of rod fracture and implant failure. As these newer rod devices become more complicated, they are also harder to bend. Thus the idea of bending to spine to meet the rod concept becomes more and more relevant, because the complicated rods become difficult or impossible to bend. By utilizing the devices of some of the embodiments described herein and lowering the pre-shaped rod into the screw heads through curved or bent towers, non-fusion growing rod devices, that can grow or lengthen as the child grows, can be easily placed into a spine in which the deformity is simultaneously reduced without the need for rod bending.

A point of novelty of some embodiments disclosed herein lies in a curved or bent tower placed on the head of the pedicle screw. However, a benefit or advantage of some embodiments of the devices and methods disclosed herein extend to a system of bent or curved towers that together are used to correct the deformity in scoliosis and deformity surgery. Mathematically, the system of curved or bent towers constitutes a transformation from a starting abnormal 3-D geometry, i.e. the deformed spine, to the final 3-D normalized spinal geometry represented by the pre-bent rod with optimized shape. Before the transformation takes place, the distal ends (pedicle screw ends) of the constellation of curved or bent tubes are configured to the abnormal geometry of the spinal deformity. At the same time, the proximal end of the constellation of curved or bent tubes are configured to the final desired 3-D geometry that represents the final corrected or normalized shape of the spine. This normalized shape is represented and characterized by the pre-bent rod. As the transformation takes place, the rod is lowered down into the constellation of curved towers, the abnormal spinal curvature transforms into the curvature of the pre-bent rod. Finally when the rod is fully inserted into the screw heads, the deformity is corrected, and the transformation is complete.

The transformation from abnormal deformity to normalized spine is a geometric topological transformation in 3 dimensional space. The transformation can be characterized by a function $N=f(D)$, where D is the 3-dimensional space comprising the deformed spine and N is the 3-dimensional space comprising the normalized spine. The function $f(\ )$ makes the transformation that corrects the deformity. The function $f(\ )$ is performed through the system of curved or bent towers and the shape of the pre-bent rod. Not only does $f(\ )$ depend on spatial coordinates but also on other factors that make the transformation safe and efficient. For example, the amount of torque or force encountered at the contact points of the rod with each "pusher" within each tower can be important to share the load between the towers as much as possible.

The system of curved or bent towers and their attributes necessary to accomplish the transformation $f(\ )$ can depend many factors. Towers of some embodiments may need to be most curved, bent, or offset at the apex of the deformity. By offset, it is meant that a proximal portion of the tower or extension is positioned at a lateral distance as compared to a distal portion of the tower or extension when the tower or extension is in an operable position. Other towers can be slightly curved, bent, or offset, or straight, or curved, bent, or offset in the opposite direction in cases where there is an "S" shaped deformity with multiple apices. Furthermore, the transformation can occur with the rod outside the body or throughout the length of the towers in a continuous manner. As a theoretical exercise, one can imagine using towers that are very long. In this case, the towers may only be bent or curved near the proximal end of the towers where the rod is first inserted. By passing the rod through the series of curves and bends, the spinal deformity can be corrected already when the rod is still far away from the distal end and even not inside the body. The rod is then passed to the distal end through straight portions of the towers that maintain the normalized spinal alignment. This feature can allow the vertebral deformity to be corrected and re-aligned without the rod directly inside the screw heads. Thus, in this way, a "correction" rod can be used outside the body to correct the deformity and then with the pedicle screw heads aligned a "permanent" rod or device can be implanted. This "permanent" device may be a growing rod or bendable rod that is not suitable to correct the deformity but is capable of maintaining the alignment after placement into the pedicle screw heads.

Preferably both the rod shaping and the configuration of curved or bent towers are computer and mathematically guided. Also preferably the rod shaping and configuration of curved or bent towers can be directed by AI and machine learning. The parameters of successful rod lowering and correction of spinal deformity is multifactorial and include patient parameters and hardware parameters. Patient parameters include age, height, weight, spinal curvature, severity of curvature, degree of flexibility of bending x-rays, bone quality, congenital abnormalities (autofusion, etc), etc. Hardware parameters can include length of the extensions, curvature of the extensions, degree of bending or lateral offset of the extensions, distribution of the curvature of the extensions (i.e., the curvature is spread out throughout the entire length of the extension versus only one or several segments of the extension), rigidity of the extensions, mobility of the screw heads (polyaxial, monoaxial, or fixed screw heads), rigidity of the rod, diameter of the rod, and/or maneuverability of the operating table or external compression devices, etc. These parameters can be directed into a computer machine learning algorithm to direct the choice of optimal curve tubes that will efficiently and safely allow the pre-bent rod to be lowered into the towers down to the screw heads. Thus through many iterations and learning, a machine learning algorithm is able to construct the N=f(D) mapping from the deformity space, D, to the normalized space, N for the general case, i.e. for all patients and under all conditions.

Also preferably the pedicle screws themselves can be inserted through a robotic means. The robotic guidance and insertion of pedicle screws is a reality and can result in accurate, safe, and efficient placement of pedicle screws. In some embodiments, the coordination between robotic placement of screws with computer algorithms that then configure the curved towers will allow the most precise and optimal correction of the vertebrae using pre-bent optimally designed rod. Currently, growing rods used in scoliosis surgery only grows in one location on the rod. Preferably, rods will be growing throughout the whole scoliosis construct with growable segments or externally controllable growable segments located inside the rod between the anchoring sites where the rod is connected to the pedicle screws. In this manner, spinal deformity can be corrected and allow for growth as the child grows in height.

In some embodiments, the curvature or bend of the towers can be adjustable. A simple example of a bendable tower is a mechanism similar to a folding ladder. The folding ladders have a bending pivot point that can change the degree and angulation of the bend, and the pivot point locks so that the ladder is stable in a variety of heights and angles. Using similar locking but bending mechanisms, a bendable tower with walls that bend but then locks can be configured in situ to match the curvature of the pre-bent rod. Basically, the towers only need to be bent so that the pre-bent rod can "fit" inside all of the towers. Once the rod is captured inside the towers, then the rod lowering process can reduce the rod into the heads of the screw. This in situ tower bending may not be optimal as the transition from deformed spine to normalized spinal alignment is not as smooth as a pre-planned smoothly curved towers. However, in some situations, such as emergency surgery where pre-planning is not possible, then such a in situ approach may be necessary and useful.

In other embodiments, towers can be bendable and adjustable, and the process of bending the tower can be computer guided. The bend in this tower can be adjusted and controlled by a computer and by definition this tower can be considered or defined as being robotic. The tower can essentially be a small robotic arm. In this manner, there are unlimited degrees of freedom in the way the deformed spine (D) is corrected into the normalized spinal alignment (N). The constellation of robotically controlled bendable towers is attached to the pedicle screws in the deformed spine. The proximal ends are robotically bent to accept the pre-bent rod that has been bent to the final normalized and optimized shape. In this case the transformation f( ) is no longer comprised of towers with fixed curvatures or bends. Instead f( ) now includes a timeline by which the curvature or bends of the towers are continuously adjustable as the rod is lowered distally into the screw heads. The time sequence of adjusting the curvature or angulation in the towers can be adjusted on the fly depending on resistive forces and torques encountered as the rod is lowered, thereby correcting the curve. This ability to robotically control the bend allows the ultimate in degrees of freedom but also makes the transformation more complicated. Computer modeling and AI would be ideal in this case to figure out the transformation.

Figure 2:
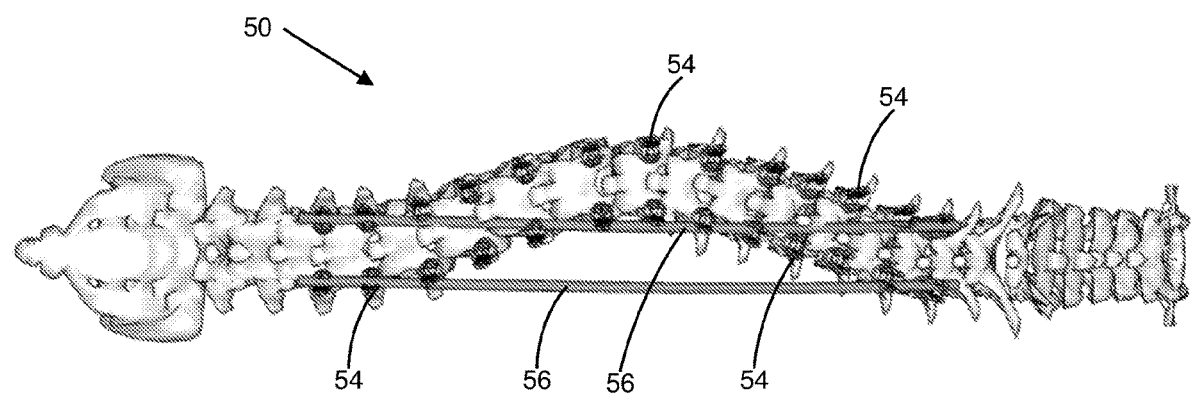
FIG. 2 is a top view of a spine having lateral curvature defects, having a plurality of pedicle screws implanted in the spine, and illustrating the degree of lateral curvature of the spine relative to a first and a second laterally straight rods.
Figure 3:
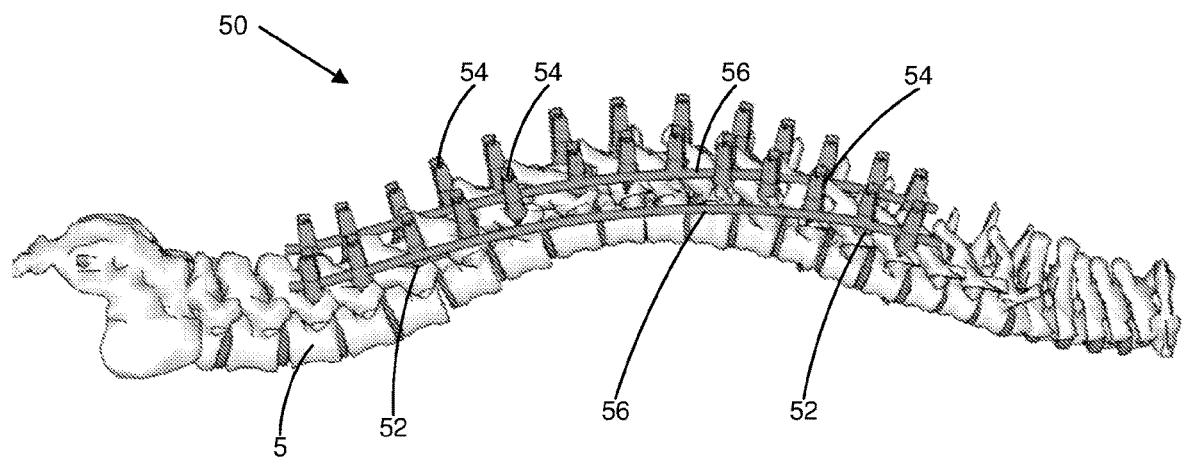
FIG. 3 is a side view of the spine shown in FIG. 2.
Figure 4:
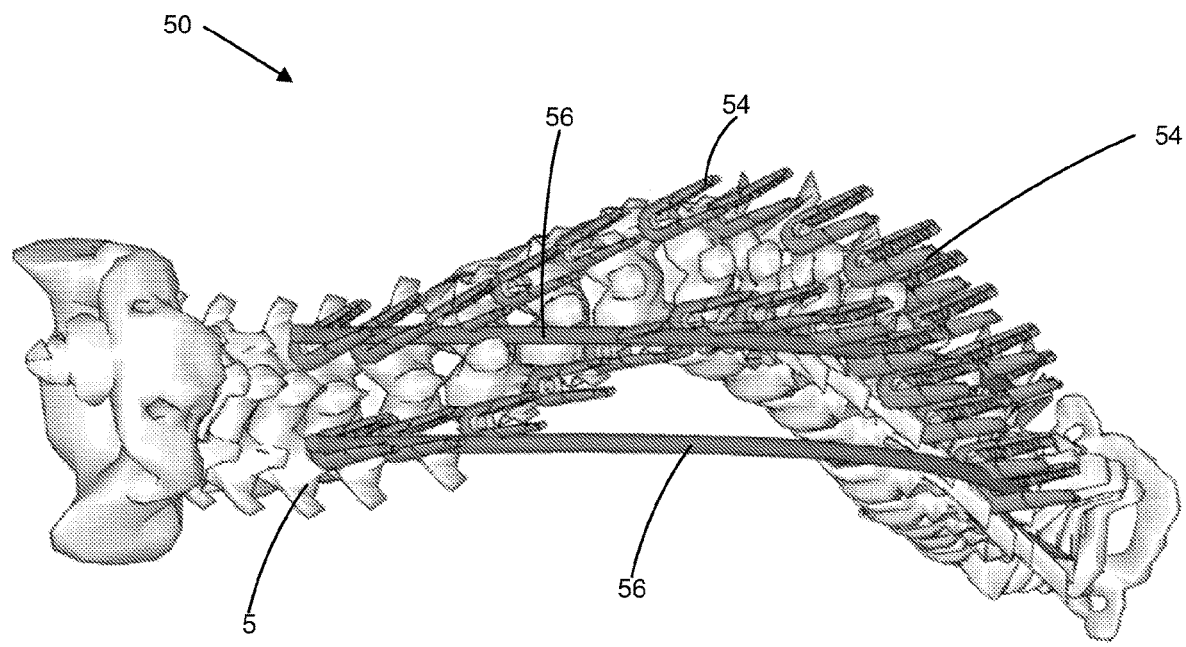
FIG. 4 is an orthogonal view of the spine shown in FIG. 2.

Some embodiments disclosed herein are directed to devices (also referred to herein as system or systems) and methods for correcting a lateral curvature of a spine, as illustrated in the figures. In some embodiments, the devices and methods are configured for treating scoliosis of a patient. FIGS. 1-4 illustrate a spine S having lateral curvature defects and having a device 50 that includes a plurality of pedicle screws 52 coupled with extensions 54 implanted in the spine. With reference to FIGS. 2-4, the device 50 can have a pair of rods 56 that are generally straight in a lateral direction (referred to as straight rods or laterally straight rods) shown in a desired location and orientation relative to the spine, but that does not fit within the heads of the pedicle screws 52 illustrated because of the curvature of the spine.

Figure 5:
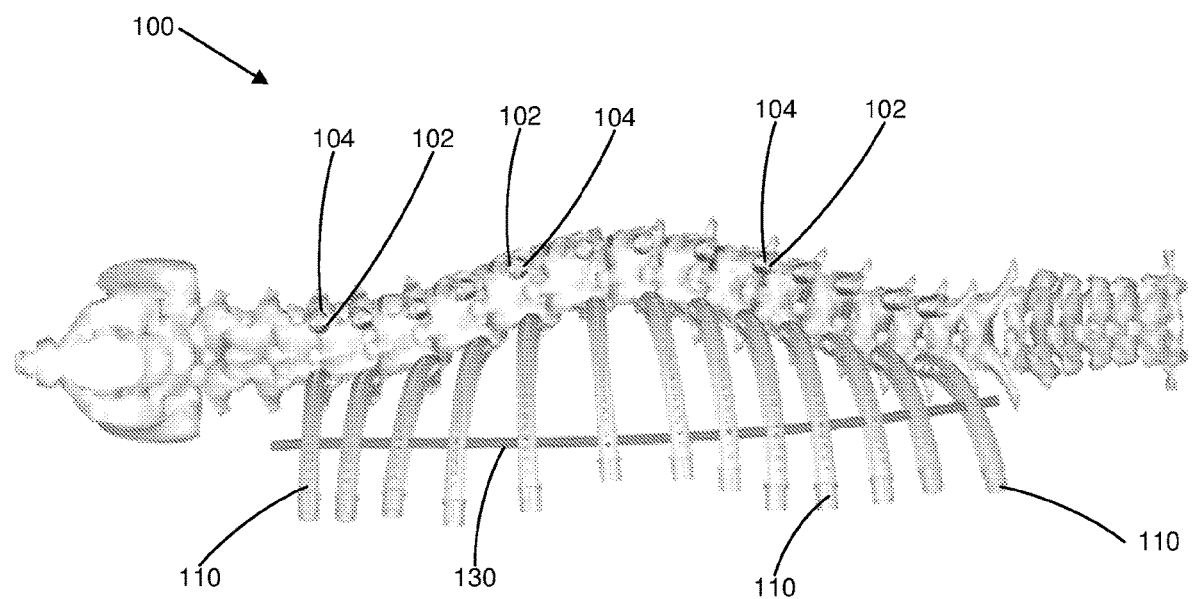
FIG. 5 shows a top view of the spine having a plurality of curved extensions engaged with the plurality of screws in the vertebra of the spine, also showing the laterally generally straight rod in engagement with the plurality of curved extensions and advanced part way toward the distal ends of the curved extensions.
Figure 6:
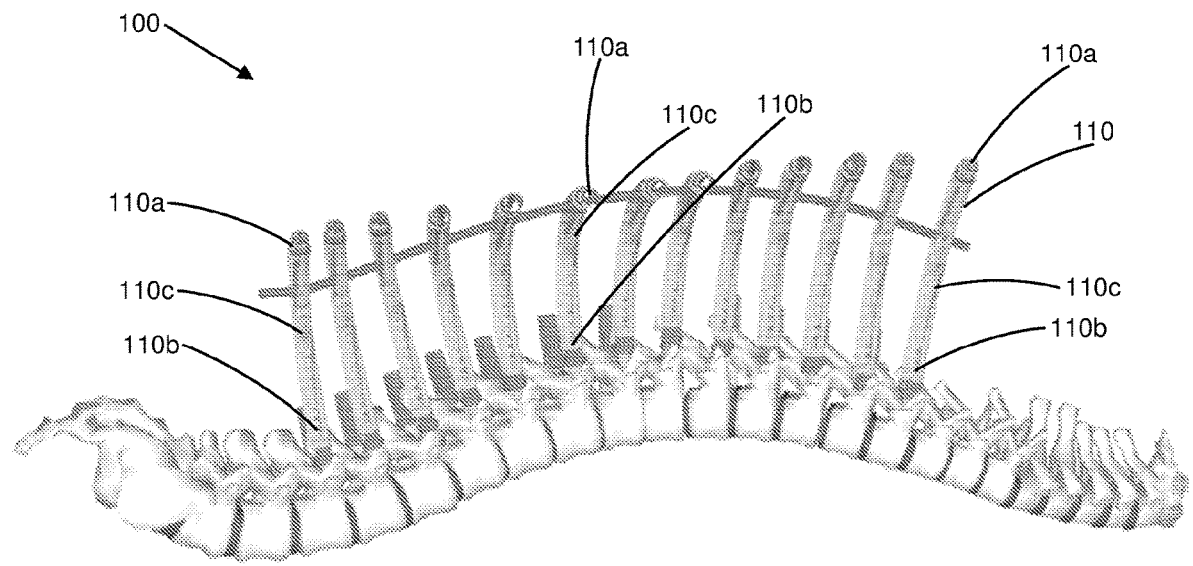
FIG. 6 shows a side view of the spine of FIG. 5 having a plurality of curved extensions engaged with the plurality of screws in the vertebra of the spine, also showing the laterally generally straight rod in engagement with the plurality of curved extensions and advanced part way toward the distal ends of the curved extensions.
Figure 7:
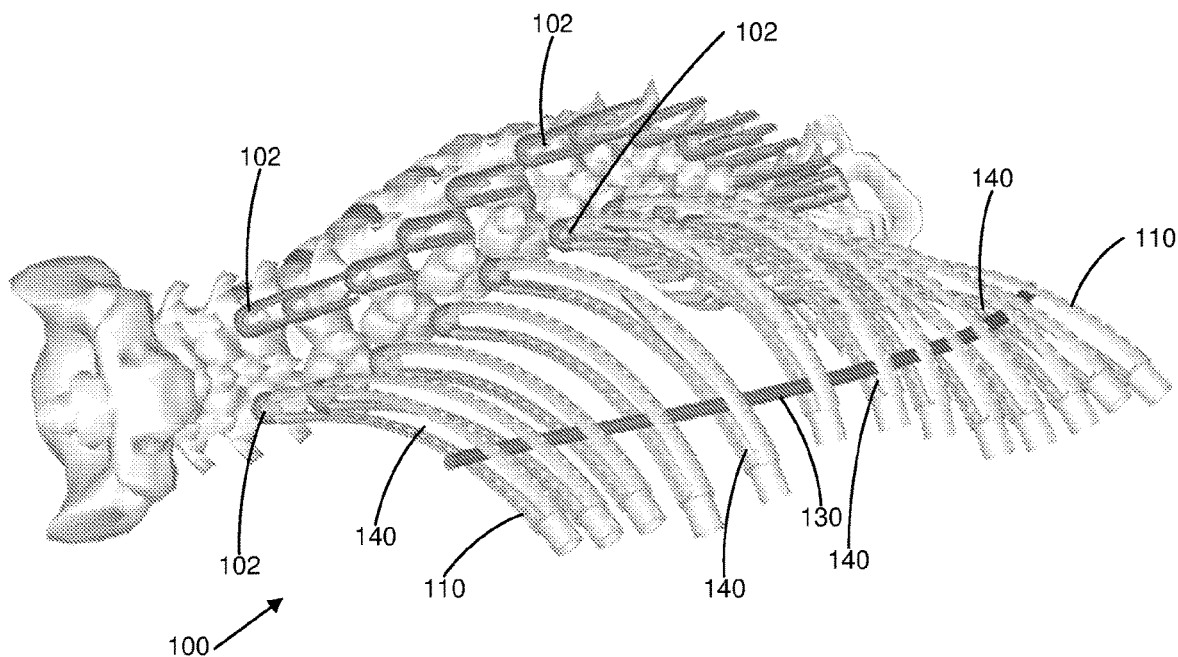
FIG. 7 shows an orthogonal view of the spine of FIG. 5 having a plurality of curved extensions engaged with the plurality of screws in the vertebra of the spine, also showing the laterally generally straight rod in engagement with the plurality of curved extensions and advanced part way toward the distal ends of the curved extensions.
Figure 8:
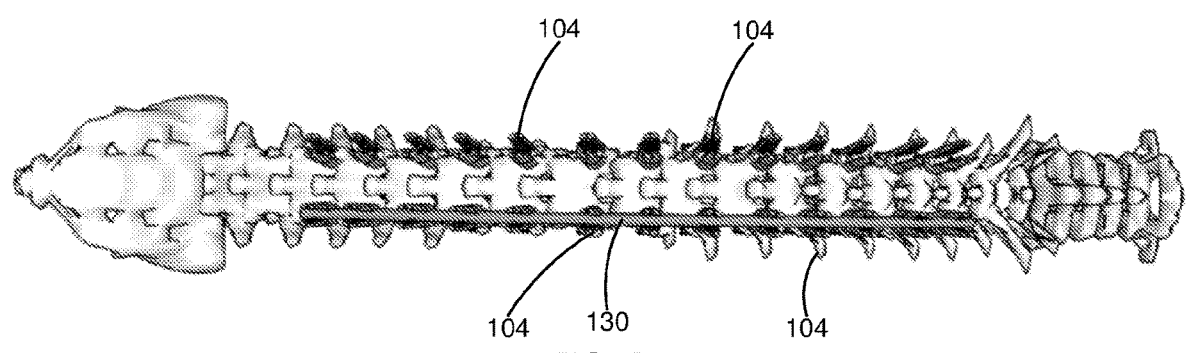
FIG. 8 shows a top view of the spine of FIGS. 1-7 after the vertebra have been laterally adjusted so as to be in lateral alignment using any of the embodiments of the systems, devices and methods disclosed herein.

Other embodiments of the devices disclosed herein, including device 100 shown in FIGS. 5-10 can include a plurality of screws 102 configured to be implanted in a plurality of vertebrae and a plurality of extensions 110 (also referred to herein as guides, guiding members, guiding elements, or towers) configured to be removably coupled with the plurality of screws 102 or a plurality of screw heads 104 coupled with the screws 102, such as shown in FIGS. 5-7. In any embodiments disclosed herein, including without limitation the embodiments of the device 100, one or more of the extensions (including, without limitation, the extensions 110) can be curved, bent, angled, offset, or otherwise. In this configuration, the extensions can be configured to receive a laterally straight rod 130 and be used to correct the deformity of the spine, as further described herein, resulting in the arrangement shown in FIGS. 8-9.

As shown in FIGS. 5-7, in some embodiments, each of the plurality of screws 102 can have a screw head 104, and each of the plurality of extensions 110 can have a proximal end portion 110a, a distal end portion 110b configured to be removably coupled with the screw head 104 of each of the plurality of screws 102, and a middle portion 110c between the proximal end portion 110a and the distal end portion 110b. The plurality of extensions of any embodiments of the devices disclosed herein can be curved, bent, angled, or otherwise offset along at least a portion thereof, for example, along all or part of the middle portion of the extensions or, in other embodiments, along an entire length of the extensions. In some embodiments, at least one of the plurality of extensions 110 can have at least one approximately straight portion along a length of extension.

Figure 9:
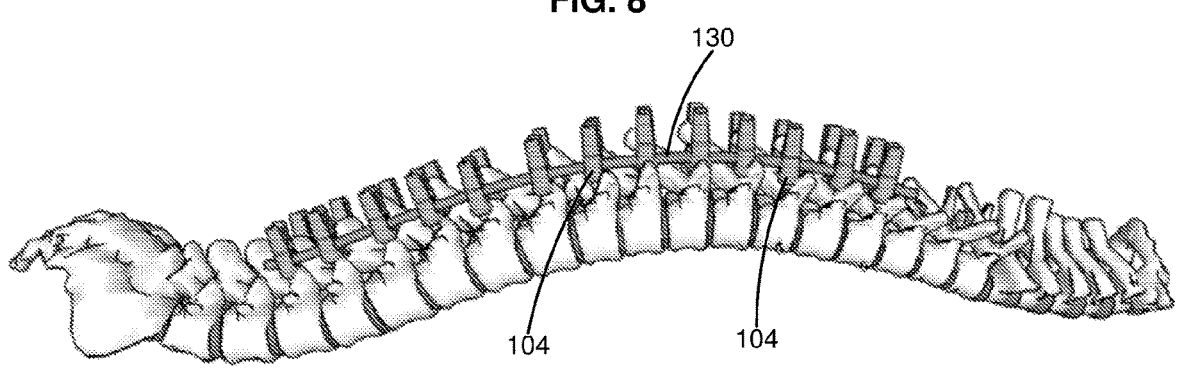
FIG. 9 shows a side view of the spine of FIG. 8.

Any of the embodiments of the devices disclosed herein can further include a rod, such as rod 130 shown in FIGS. 5-9 that can be configured to be coupled with or selectively engaged with the plurality of screw heads 104, wherein the device 100 can be configured such that the rod 130 can be guided along the plurality of extensions 110 from the proximal end portions 110a of the plurality of extensions 110 toward the distal end portions 110b of the plurality of extensions 110 and into engagement with the plurality of screws 102. In some embodiments, as shown in FIG. 9, for example, the rod 130 can be bent and/or curved into a desired configuration in the sagittal plane (or other non-lateral direction) while still having a generally laterally straight shape, the non-lateral curvature of the rod generally matching the desired post-operative curvature of the spine.

In any embodiments of the devices disclosed herein, extensions 110 of varying curvature and/or length can be selected and can be coupled with the screw heads 104 so that the distal end portions 110b of the extensions are engaged with the vertebra in the pre-operative position of the vertebra, and so that the proximal end portions 110a of the extensions can be approximately or generally aligned. For example and without limitation, the proximal end portion 110a of each of the extensions 110 can be configured so that, when the extensions 110 are in an operable state, for example as shown in FIGS. 5-7, the proximal end portions 110a of the extensions 110 can be in close enough alignment that a laterally straight and generally rigid rod can be engaged with a proximal end portion 110a of each of the extensions 110 or a slot 140 of each of the extensions 110 while the distal end portions 110b of the extensions follow the shape and/or position of the laterally curved spine. In this arrangement, as the laterally straight and substantially rigid rod 130 is moved through the slots 140 of the extensions 110 toward the distal end portions 110b of the extensions 110, the rigidity and linear straightness of the rod 130 will cause the distal end portions 110b of the extensions 110 and, hence, the screws 102 and the vertebra with which the screws are engaged, to move toward a linear centerline of the spine, or to cause the vertebrae to move into general alignment.

Thus, the devices and methods of any embodiments described herein, including without limitation, the embodiments of the device 100, can be configured to move one or more vertebra in a lateral direction and into general lateral alignment as the rod 130 is advanced toward the distal end portions 110b of the plurality of extensions 110 and into engagement with the plurality screw heads 104. Further, the devices and methods can be configured such that the rod 130 can be simultaneously advanced down the plurality of extensions 110 by incrementally advancing the rod 130 toward the distal end portion 110b of each of the plurality of extensions 110. The devices and methods of any embodiments, including without limitation, the embodiments of the device 100, can be configured to move one or more vertebra toward a lateral centerline of the spine as the rod 130 is advanced toward the distal end portions 110b of the plurality of extensions 110.

In any embodiments disclosed herein, the rod 130 and the other components of the device 100 can be made from any suitable materials and can have any features of any conventional spinal implant devices. Further, in some embodiments, the rod 130 can be generally straight in the lateral direction. The rod 130 can be curved in the sagittal plane, as described above.

Figure 10:
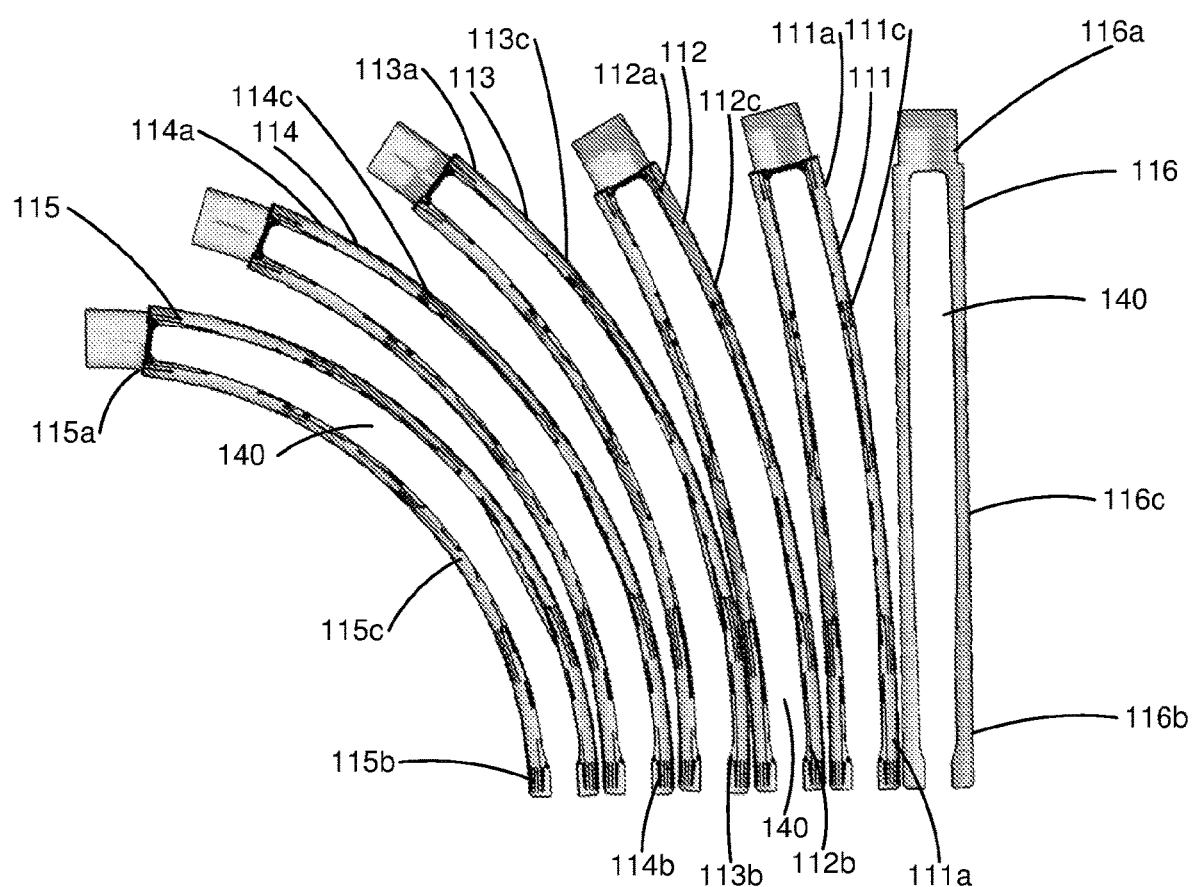
FIG. 10 shows a side view of a plurality of extensions of an embodiment of a system for treating a lateral curvature of the spine.
Figures 11A, 11B:
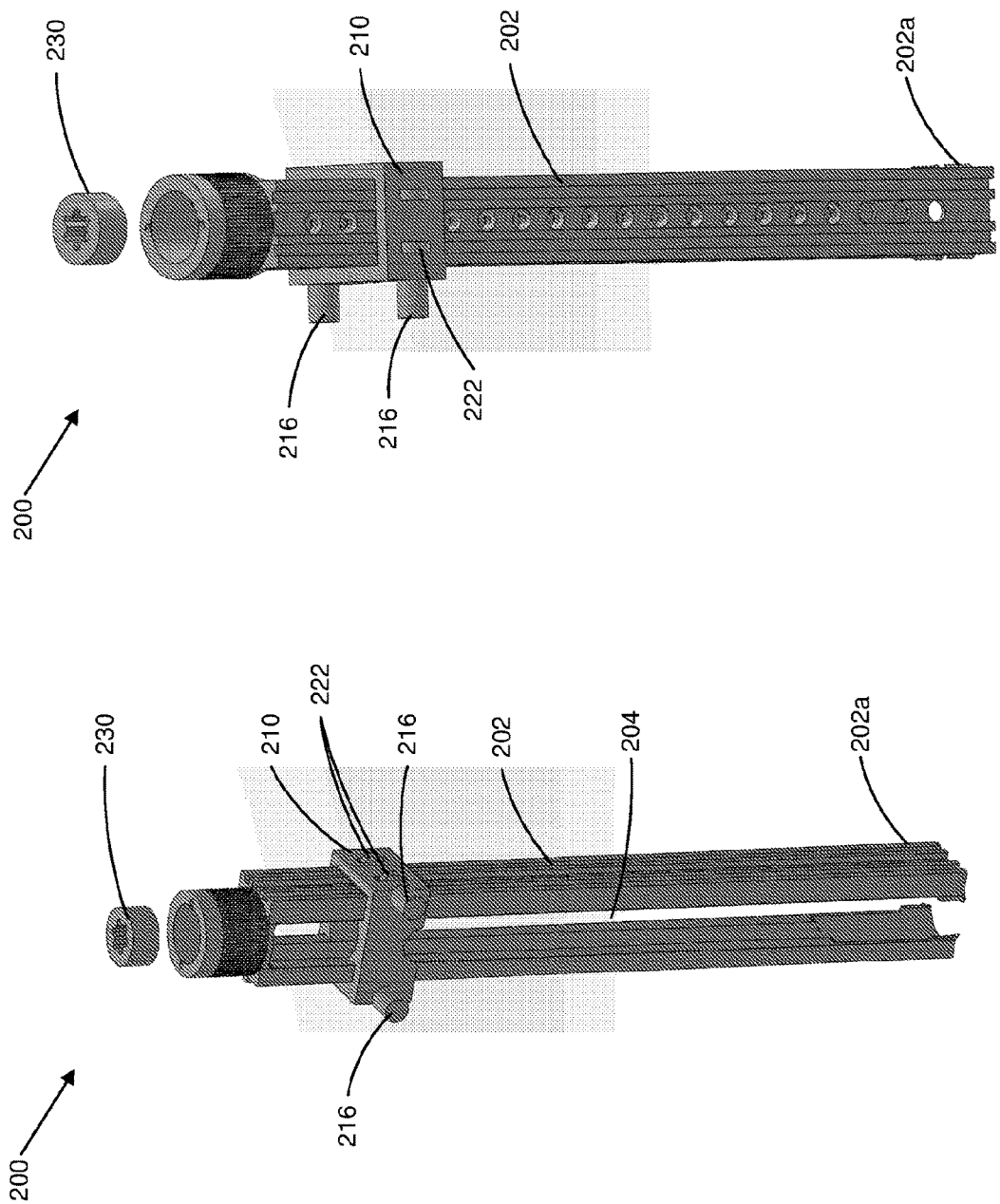
FIGS. 11A-11G show an embodiment of a rod lowering device that can be used with any of the systems or devices disclosed herein for treating the spine.
Figure 11D:
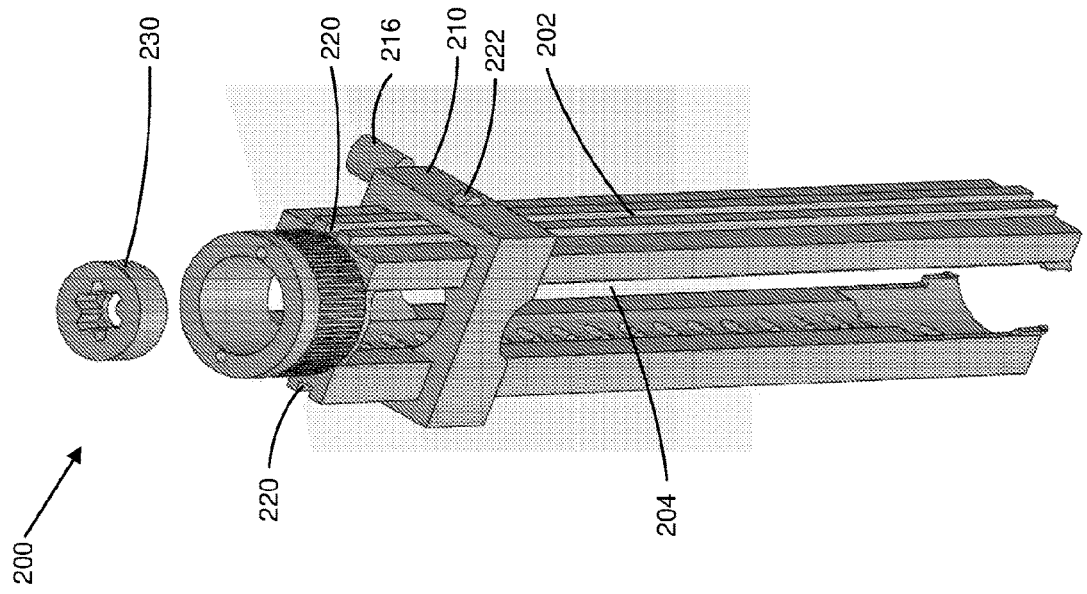
Figure 11C:
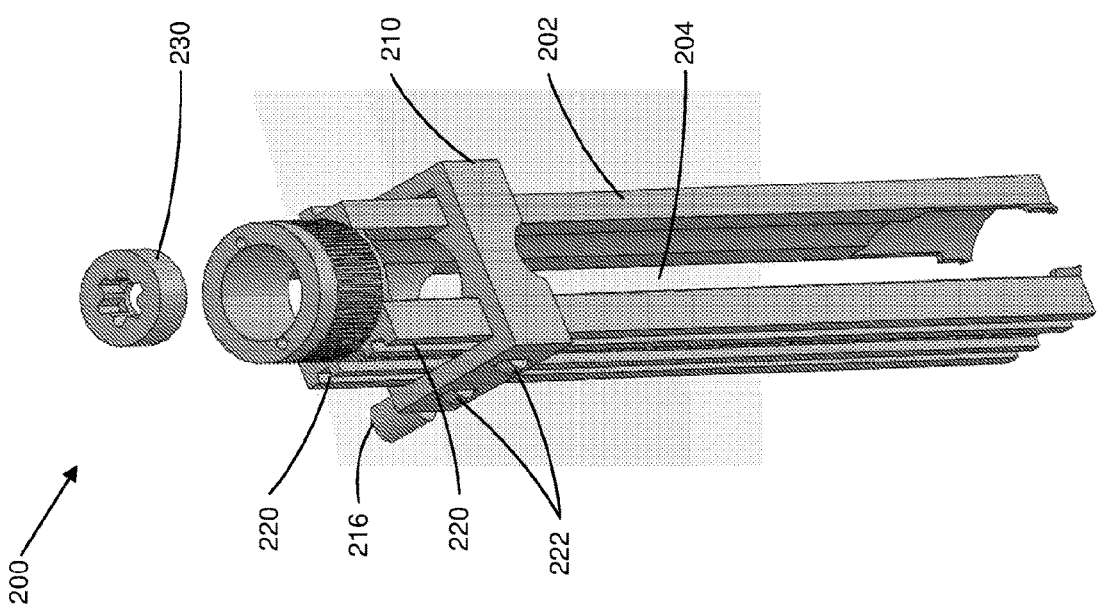
Figure 11F:
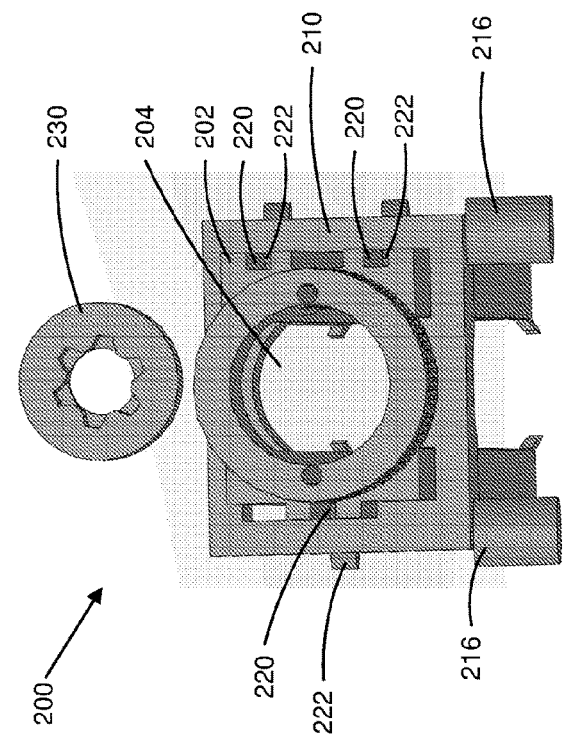
Figure 11G:
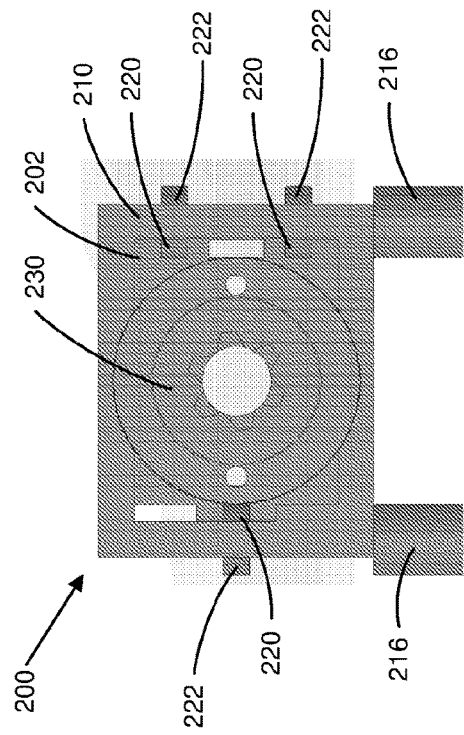
Figure 11E:
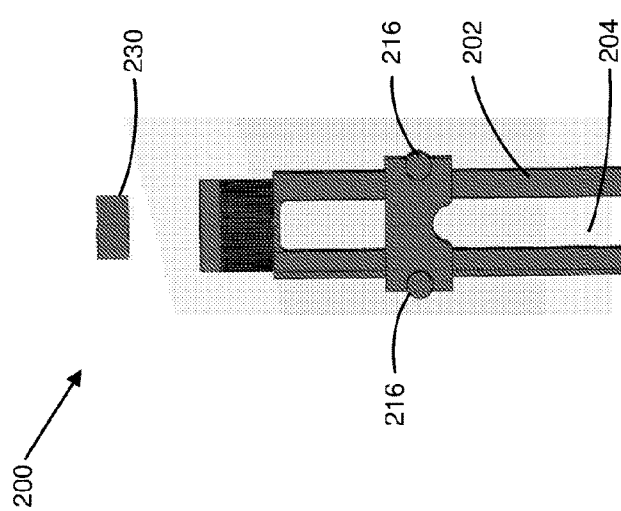

Additionally, to accommodate a variety of different spinal conditions, the device of any embodiments disclosed herein, including device 100, can have a plurality of extensions 110 having varying lengths and/or varying curvatures, bends, or offsets. FIG. 10 shows an embodiment of a plurality of extensions 110 that can be used with any embodiments of the devices disclosed herein. FIG. 10 shows a first extension 111, a second extension 112, a third extension 113, a fourth extension 114, a fifth extension 115, and a sixth extension 116. The first extension 111 can have a proximal end portion 111a, a distal end portion 111b, and a middle portion 111c extending between the proximal end portion 111a and the distal end portion 111b. The second extension 112 can have a proximal end portion 112a, a distal end portion 112b, and a middle portion 112c extending between the proximal end portion 112a and the distal end portion 112b. The third extension 113 can have a proximal end portion 113a, a distal end portion 113b, and a middle portion 113c extending between the proximal end portion 113a and the distal end portion 113b. The fourth extension 114 can have a proximal end portion 114a, a distal end portion 114b, and a middle portion 114c extending between the proximal end portion 114a and the distal end portion 114b. The fifth extension 115 can have a proximal end portion 115a, a distal end portion 115b, and a middle portion 115c extending between the proximal end portion 115a and the distal end portion 115b. The sixth extension 116 can have a proximal end portion 116a, a distal end portion 116b, and a middle portion 116c extending between the proximal end portion 116a and the distal end portion 116b. The proximal end portions of some embodiments of the first extension 111, second extension 112, third extension 113, fourth extension 114, fifth extension 115, and the sixth extension 116 can be curved, bent, angled, or otherwise offset from the distal end portions thereof.

In any embodiments, the middle portion 111c of the first extension 111 can have a first curvature, bend, angle, or offset, the middle portion 112c of the second extension 112 can have a second curvature, bend, angle, or offset, and the second curvature, bend, angle, or offset can be greater than or otherwise different than the first curvature, bend, angle, or offset. The middle portion 113c of the third extension 113 can have a third curvature, bend, angle, or offset, and the third curvature, bend, angle, or offset can be greater than or otherwise different than the second curvature, bend, angle, or offset. The middle portion 114c of the fourth extension 114 can have a fourth curvature, bend, angle, or offset, and the fourth curvature, bend, angle, or offset can be greater than or otherwise different than the third curvature, bend, angle, or offset. The middle portion 115c of the fifth extension 114 can have a fifth curvature, bend, angle, or offset, and the fifth curvature, bend, angle, or offset can be greater than or otherwise different than the fourth curvature, bend, angle, or offset. The sixth extension can have a generally straight profile. In some embodiments, the device can be configured such that the plurality of extensions 110 can have at least four different curvatures, bends, angles, offsets, and/or lengths. In some embodiments, the device can wherein the plurality of extensions 110 can have at least five different curvatures, bends, angles, offsets, and/or lengths, or from five to ten different curvatures, bends, angles, offsets, and/or lengths.

Additionally, in any embodiments disclosed herein, the distal portions 110b of the extensions 110 can be straight. The distal portions 110b of any of the extensions described herein may be axially aligned with the screw 102 and/or screw head 104, for example parallel with and coaxial with the threaded screw body of the screw and rigidly coupled to or relative to the screw and/or screw head. In any embodiments disclosed herein, a distal end portion of at least one of the plurality of extensions (including but not limited to extensions 110) can be flexibly coupled with the corresponding screw and/or screw head in any embodiments disclosed herein. For example and without limitation, the system can be configured such that at least one of the plurality of extensions is (or, in other embodiments, all of the plurality of extensions are) configured to rotate in a lateral direction (or at least in a lateral direction) relative to a corresponding screw that the extension is coupled with, wherein the lateral direction is the direction in a plane that is perpendicular to a centerline of the spine. For example and without limitation, the extension can be configured to rotate relative to an axial centerline of a corresponding screw within a range of 20 degrees or approximately 20 degrees, or within a range of 10 degrees or approximately 10 degrees, in a lateral direction, wherein the lateral direction is the direction in a plane that is perpendicular to a centerline of the spine. In any embodiments, the system can be configured wherein the distal end portion of each of the plurality of extensions is configured to be rigidly coupled with a corresponding one of the plurality of screws and/or a corresponding one of the plurality of screw heads such that at least the distal end portion of each of the plurality of extensions is axially aligned with the corresponding screw and/or screw head and is inhibited from rotating relative to each of the plurality of screws in an operable position. Further, the distal portions 110b of the extensions 110 can have a length that is greater than or equal to a length from the distal end of the extension to the surface of the patient's skin such that the distal portion 110b of each of the plurality of extensions 110 extends at least to the surface of the patient's skin. In this configuration, the portion of the extensions 110 that are within the patient's body can be straight and such that any curve, bend, angle, or offset of the extensions occurs outside of the patient's body. Further, in any embodiments disclosed herein, the proximal and/or distal portions can be curved, bent, angled, or otherwise offset.

Additionally, any embodiments of the extensions 110 can have a discontinuous curve along a length thereof. For example, a proximal portion of the an extension 110 can be curved, an adjacent portion can be generally straight, followed by another curved portion adjacent to or in the distal end portion. Further, any embodiments can have multiple bends along a length of the extension, or multiple bends separated by straight sections and/or multiple angled regions along a length of the extension, or a combination of curves, bends, and/or angles along a length thereof. Further, any embodiments of the extensions 110 can be curved in multiple directions. For example and without limitation, any embodiments of the extensions can be curved in one direction in a first portion of the extension and then curved in another direction (for example, the opposite direction) in a second portion of the extension. Any embodiments can be curved to have an "S" shape.

In some embodiments, the plurality of extensions 110 each can have a slot 140 therein extending from the proximal end portion 110a of each of the plurality of extensions 110 toward the distal end portion 110b of each of the plurality of extensions 110, wherein the slot 140 of each of the plurality of extensions 110 can be configured to slidably receive the rod 130 therein such that the rod 130 can be guided toward the plurality of screw heads 104 using the slots 140 of the plurality of extensions 110. For example, FIGS. 5-7 show a rod 130 being advanced down the slots 140 of a plurality of extensions 110 toward a distal end portion 110b of such extensions 110. A similar arrangement can be used to slide a rod 130 down toward the second set of screws 102 shown in FIGS. 5-7 (the extensions 110 for the second set of screws 102 being omitted for clarity). The first and second rods 130 can be advanced approximately simultaneously or incrementally to reduce the loading on any one of the screws 102 and extensions 110.

In some embodiments, the device 100 can have a plurality of push elements or inserts (not shown) configured to couple with the plurality of extensions 110 and to selectively move the rod 130 down toward the distal end portions 110b of the plurality of extensions 110 toward the plurality of screw heads 104 as the plurality of push elements are advanced toward the distal end portions 110b of the plurality of extensions 110. The push elements are one nonlimiting example of a mechanism and method for advancing the rod 130 incrementally toward the distal end portions 110b of the plurality of extensions 110. The push elements or inserts can be configured to move down a slot 140 or opening formed in the extensions 110, or can be configured to move down along an outside surface of the extensions 110 to move the rod 130 toward the distal end portion 110b of the extensions 110. The push elements can, therefore, be coupled with or engage with the rod 130 and the extensions 110 to allow the surgeon or an automated machine (such as, without limitation, a surgical robot) to selectively and incrementally (and independently) advance the rod 130 toward each of the distal end portion 110b portions of the extensions 110. In any embodiments, the push elements can be selectively moved in a proximal direction toward the proximal end portion 110a of the extensions 110 to allow the rod 130 to move proximally, for readjustment of the rod 130 or otherwise. A flexible shaft tool can be used to either push or rotate the push elements toward the distal end portion 110b of the extensions 110.

In some embodiments, the plurality of push elements and/or other components of the device used to advance the rod 130 can each be selectively biased against moving toward the proximal end portion 110a of the plurality of extensions 110 as the plurality of push elements or other components are advanced toward the distal end portions 110b of the plurality of extensions 110. In some embodiments, the device 100 can have a plurality of threaded push elements configured to threadedly engage with the plurality of extensions 110 and to selectively move the rod 130 down toward the distal end portions 110b of the plurality of extensions 110 toward the plurality of screw heads 104 as the plurality of push elements are threadedly advanced toward the distal end portions 110b of the plurality of extensions 110. In any embodiments, the plurality of threaded push elements can be a plurality of screws 102.

In some embodiments, the plurality of extensions 110 can have a slot 140 therein extending from the proximal end portion 110a of each of the plurality of extensions 110 toward the distal end portion 110b of each of the plurality of extensions 110. The slot 140 can extend all the way to the screw head 104 of each of the plurality of screws 102 that is adjacent to the distal end portion 110b of the extensions 110). The slot 140 of each of the plurality of extensions 110 can be configured to slidably receive the rod 130 therein such that the rod 130 can be guided toward the plurality of screw heads 104 using the slots 140 of the plurality of extensions 110. A plurality of push elements can be configured to engage with the slot 140 of each of the plurality of extensions 110. For example and without limitation, the slot 140 of each of the plurality of extensions 110 can have internal threads therein configured to threadedly engage with a plurality of threaded push elements that can be threadedly advanced in the slots 140 toward the distal end portions 110b of the plurality of extensions 110 to cause the rod 130 to be advanced toward the plurality of screw heads 104.

In any embodiments, the device 100 can be configured to selectively prevent the rod 130 from moving toward the proximal end portion 110a of each of the plurality of extensions 110 as the rod 130 is being advanced toward the distal end portion 110b of each of the plurality of extensions 110. In some embodiments, the plurality of guide elements can be configured to couple with the rod 130 and to slide along the plurality of extensions 110 from the proximal end portion 110a of each of the plurality of extensions 110 toward the distal end portion 110b of each of the plurality of extensions 110 to guide the rod 130 toward the plurality of screw heads 104. In any embodiments, the device can further have a plurality of locking caps or other suitable components or features each configured to engage with the screw head of each of the plurality of screws 102 and to secure the rod 130 to each of the screw heads 104.

In some embodiments, with reference to FIG. 7, the plurality of screws 102 can include a first plurality of screws 102 and a second plurality of screws 102. Any embodiments of the device 100 can be configured such that the first plurality of screws 102 will each be implanted in a plurality of vertebrae adjacent to each of the second plurality of screws 103. For example, the first plurality of screws 102 can be positioned on one side of the vertebrae and the second plurality of screws 102 can be positioned on a second side of the vertebrae.

The plurality of extensions 110 can include a first plurality of extensions 110 and a second plurality of extensions 110, wherein each of the first plurality of extensions 110 can be configured to be removably coupled with the screw heads of each of the first plurality of screw 102 on the first side of the vertebrae, and each of the second plurality of extensions 110 can be configured to be removably coupled with the screw head of each of the second plurality of screws 102 on the second side of the vertebrae.

Additionally, the device of any embodiment disclosed herein, including without limitation device 100, can have a first rod 130 and a second rod 130, and the device can be configured such that the first rod 130 can be guidable along the first plurality of extensions 110 from the proximal end portions 110a of the first plurality of extensions 110 toward the distal end portions 110b of the first plurality of extensions 110 and into engagement with the first plurality of screws 102, and such that the second rod 130 can be guidable along the second plurality of extensions 110 from the proximal end portions 110a of the second plurality of extensions 110 toward the distal end portions 110b of the second plurality of extensions 110 and into engagement with the second plurality of screws 102.

Additionally, the device of any embodiment disclosed herein, including without limitation device 100, can have a first screw having a first screw head, a second screw having a second screw head, and a third screw having a third screw head, each implantable into a vertebra of a patient or subject. The device of any embodiment disclosed herein can also have a first extension having a proximal end portion 110a, a distal end portion 110b configured to be removably couplable with the first screw head, and a middle portion 110c between the proximal and distal end portions 110b, wherein at least a portion of the first extension can be curved. Some embodiments of the device can also have a second extension having a proximal end portion 110a, a distal end portion 110b configured to be removably couplable with the second screw head, and a middle portion 110c between the proximal and distal end portions 110b, wherein at least a portion of the second extension can be curved. Some embodiments of the device can also have a third extension having a proximal end portion 110a, a distal end portion 110b configured to be removably couplable with the third screw head, and a middle portion 110c between the proximal and distal end portions 110b, wherein at least a portion of the third extension can be curved.

FIGS. 11A-11G and FIGS. 12A-12G show an embodiment of a straight rod lowering device 200 and a curved rod lowering device 300, respectively, that can be used with any of the systems or devices disclosed herein for treating the spine. Therefore, in any embodiments, the rod lowering devices 200, 300 can be straight as in FIGS. 11A-11G, curved as in FIGS. 12A-12G, bent, offset, or otherwise not straight.

In some embodiments of the systems disclosed herein, one of the rod lowering devices 200, 300 would be positioned on each extension, or a plurality of the extensions, of any of the systems disclosed herein. The rod lowering devices 200, 300 could be configured to be advanced on tracks, channels, grooves, or other features located on outside surface of the extensions, including straight, angled, and/or curved extensions. Additionally, the rod lowering devices 200, 300 can be configured to work with surgical robotic arms or end effectors coupled therewith so that all or a plurality of the rod lowering devices 200, 300 can be used simultaneously to lower the rod tow the screw heads. In this configuration, the process of rod lowering can be a concerted, coordinated effort that is computer guided and programmed Additionally, in any embodiments, the rod lowering devices 200, 300 can have torque or force sensors, for example and without limitation, on the contact members 210, 310, to provide feedback regarding the amount of force being applied to the contact members 210, 310 and, hence, the rod. This can be used to prevent excessive torque or pressure at any part of the rod. The goal of some embodiments is to push the rod down with as even torque distributed amongst all the towers as possible.

Some embodiments of the systems disclosed herein can include a plurality of rod lowering devices 200, 300 to assist with a lowering of a rod toward the plurality of screw heads, and to move one or more vertebra in a lateral direction as the rod is lowered down toward a distal end of the plurality of rod lowering devices. In some embodiments, each of the rod lowering devices 200, 300 can include a body portion 202, 302 having a passageway 204, 304 therethrough, the passageway 204, 304 being configured to receive a corresponding one of the plurality of extensions (including, without limitation, extensions 110, 111-116, or otherwise) therein as the rod lowering devices 200, 300 are passed over the plurality of extensions, and a contact member 210, 310 configured to translate along a length of the body portion 202, 302 of the rod lowering device 200, 300. The contact member 210, 310 can be configured to removably couple with the rod (for example and without limitation, rod 56, rod 130, or otherwise) that is configured to be coupled with the plurality of screw heads. In some embodiments, each of the body portions 202, 302 can have a distal end portion 202a, 302a configured to be removably coupled with a corresponding one of a screw, a corresponding one of a screw head, and/or a distal portion of a corresponding one of an extension.

Further, in some embodiments, the rod lowering devices 200, 300 can be configured to move the rod toward the screw heads as the contact members 210, 310 are moved toward the screw heads. In other words, in some embodiments, the contact members 210, 310 can be configured to couple with the rod so that, as the contact members 210, 310 are moved toward the distal ends 202a, 302a of the body portions 202, 302 of the rod lowering devices 200, 300, the rods will be simultaneously moved toward the distal ends 202a, 302a of the body portions 202, 302 of the rod lowering devices 200, 300. The contact member 210, 310 can be configured to slide, roll, or otherwise translate along the body portion 202, 302. The contact members 210, 310 can have one or more pins or projections 216, 316 that can be grasped or otherwise contacted to move the contact member 210, 310. For example and without limitation, a robotic arm or component affixed to a robotic arm can couple with the one or more projections 216 so that a movement of the plurality of contact members 202, 302 can be controlled by one or more robotic arms.

In some embodiments, the body portion 202, 302 of one or more of the rod lowering devices 200, 300 can have one or more grooves 220, 320 along the length thereof, wherein the grooves 220, 320 are each configured to receive a portion of the contact member 210, 310 therein as the contact member 210, 310 is advanced along the length of the body portion 202, 302 of the respective rod lowering device 200, 300. The grooves 220, 320 can be configured to receive a projection or a wheel 222, 322 of the contact member 210, 310 therein as the contact member 210, 310 is advanced along the length of the body portion 202, 302 of the respective rod lowering device 200, 300.

In any embodiments disclosed herein, the passageway 204, 304 can be threaded along a length thereof, and the rod lowering devices 200, 300 can have a threaded cap 230, 330 configured to be threadedly advanced down the passageway 204, 304 toward the screw head. The cap 230, 330 can be configured to threadedly couple with each of the plurality of screw heads to secure the rod to the plurality of screw heads.

Figure 13:
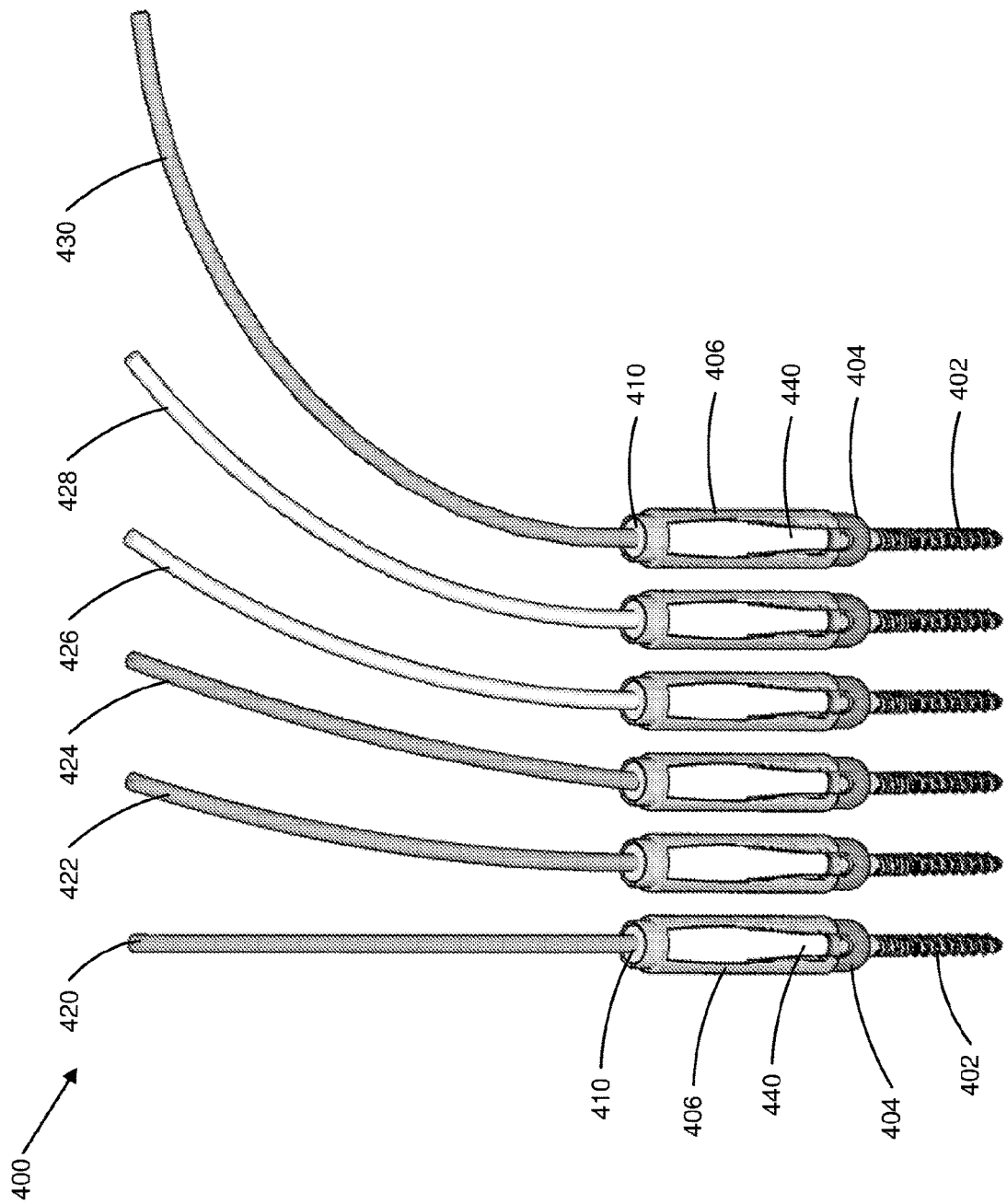
FIG. 13 is an isometric view of an embodiment of a system or a portion of a system for treating a lateral curvature of a spine.
Figure 14A:
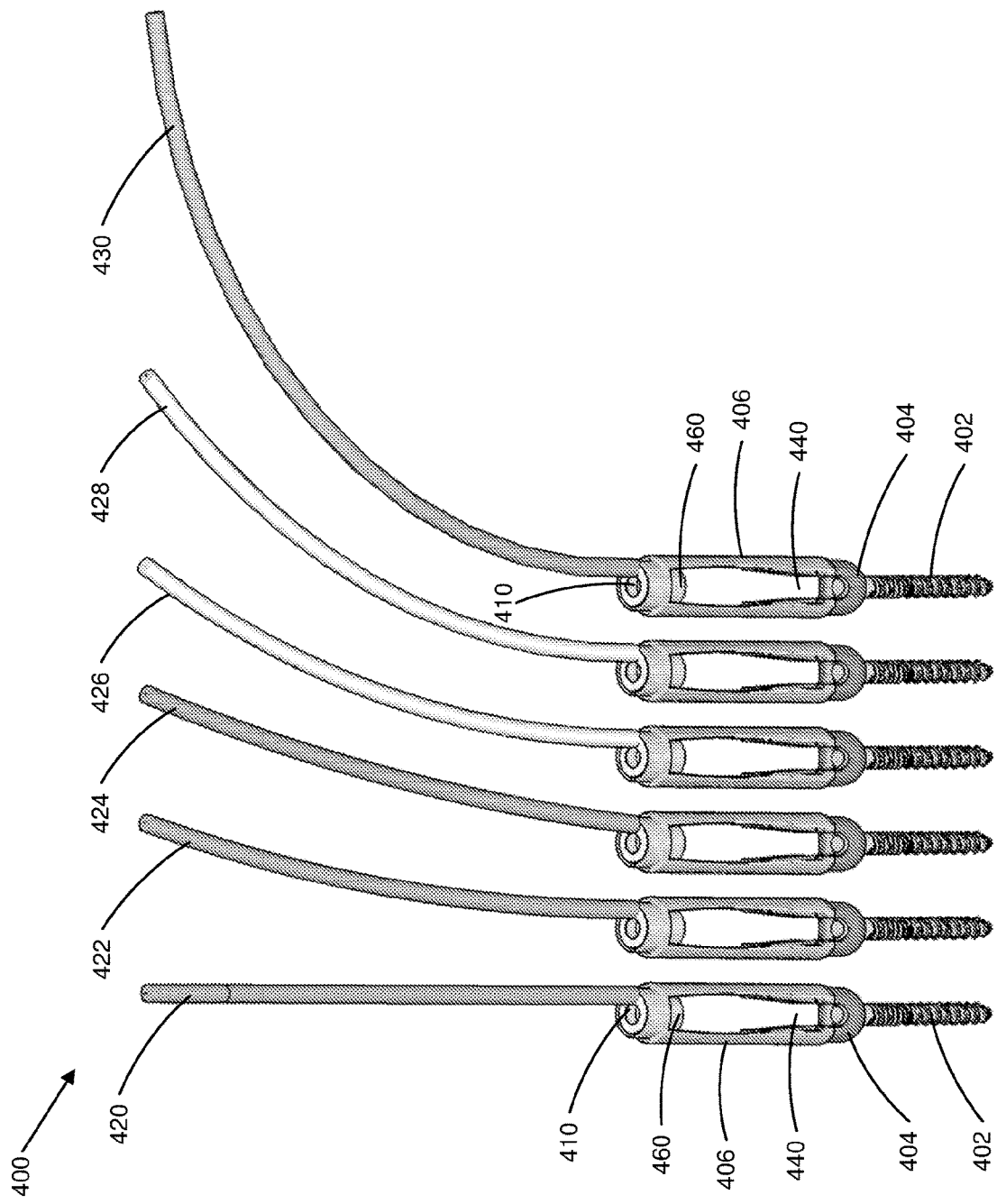
FIG. 14A is an isometric view of an embodiment of a system or a portion of a system for treating a lateral curvature of a spine.
Figure 14C:
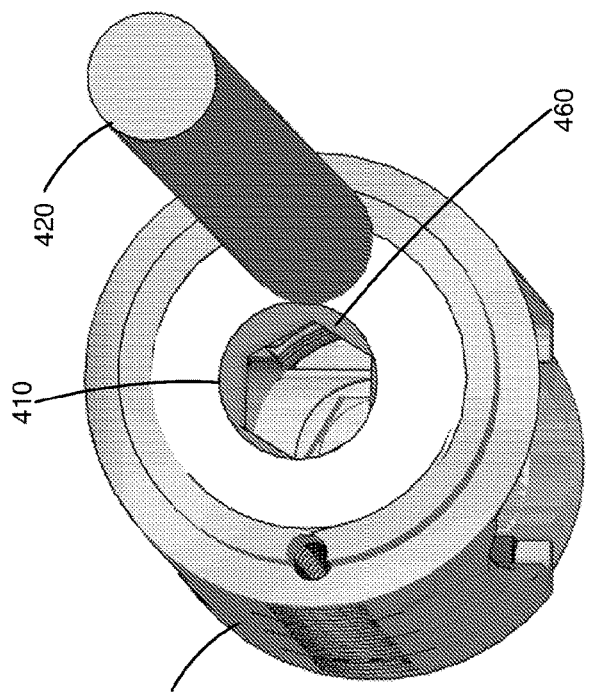
FIG. 14C is a side view of a portion of the embodiment shown in FIG. 14A.
Figure 14B:
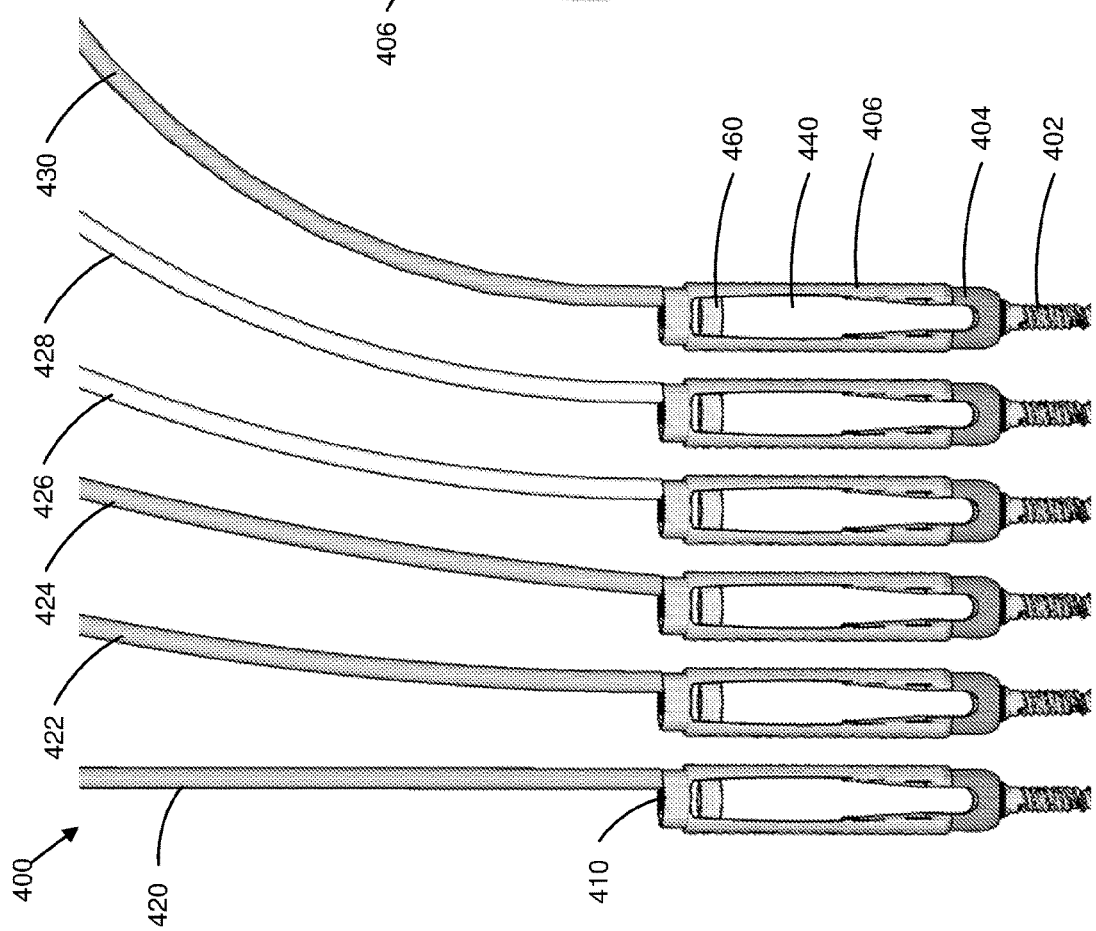
FIG. 14B is a side view of the embodiment of the system or portion of the system shown in FIG. 14A.

FIG. 13 is an isometric view of an embodiment of a system 400 or a portion thereof for treating a lateral curvature of a spine. FIGS. 14A-14C show another embodiment of a system 400 or a portion thereof for treating a lateral curvature of a spine. System 400 can include a plurality of screws 402, a plurality of screw heads 404 coupled with the plurality of screws 402, and a plurality of extensions 406 that can be removably coupled with the plurality of screws 402 and/or the plurality of screw heads 404. The extensions 406 (which are also referred to herein as towers or short towers) can have an opening 410 therein that can be in a proximal end portion of the extensions 406. In any embodiments, the system 400 can include a first guiding member 420, a second guiding member 422, a third guiding member 424, a fourth guiding member 426, a fifth guiding member 428, and/or a sixth guiding member 430. In some embodiments, the guiding members 420-430 can be generally rigid and be configured to communicate a shear force along a length thereof to the extensions when the guiding members are laterally displaced so as to laterally move or displace the respective vertebra as the guiding members are laterally displaced.

Any of the guiding members 420-430 can have straight trajectories (for example, as in the first guiding member 420), curved trajectories (for example, as in the second through sixth guiding members 422-430), bent trajectories, or otherwise offset trajectories wherein a distal end portion of the guiding member (i.e., the end portion closest to the extensions 406) is in a different lateral position as compared to a proximal end portion of the guiding member when the guiding member and the other components of the system are in an operable position in a patient's body. Other embodiments can have any desired number of each of the guiding members 420-430, or guiding members having other trajectories.

The guiding members 420-430 can be coupled with the proximal end portions of the extensions 406. For example and without limitation, the guiding members 420-430 can be coupled with or advanced into the openings 410 of the extensions 406, as shown in FIG. 13. In other embodiments, as shown in FIGS. 14A-14C, the guiding members 420-430 can be coupled with the proximal end of the extensions 406 in a position that is laterally offset from the opening 410 of each guiding member 420-430. In this configuration, the opening 410 of each extension 406 will not be covered by the guiding member 420-430, thereby allowing a tool to be passed through the opening 410 to engage the cap 460 that can be preloaded in each extension 406 to turn and threadedly advance the cap 460 toward the screw head 404. In any embodiments disclosed herein, any of the guiding members 420-430 can be solid, hollow (such as a tube), or otherwise, and can have any desired cross-sectional shape, including circular, non-circular, square, ovular, polygonal, or otherwise.

In any embodiments disclosed herein, the system 400 can be configured such that the guiding members 420-430 are positioned completely outside of a patient's body, or above the skin level of a patient's body, when the screws 402 are implanted in an operable position in the patient's spine. The guiding members 420-430 can be configured to guide an external rod or alignment element (not shown) toward the distal ends of the guiding members 420-430. The alignment element can be configured to cause the screws 402 and the vertebrae that the screws 402 are implanted into to move toward a lateral centerline of the patient's spine as the alignment element is advanced toward the distal ends of the guiding members 420-430, thereby moving the respective vertebrae into approximate lateral alignment or at least moving the vertebrae closer to lateral alignment. The alignment element or external rod can be generally straight in a lateral direction, but have a curvature in the sagittal plane that generally matches a curvature of the patient's spine in the sagittal plane. The guiding members 420-430 can be configured to facilitate a movement or translation of the alignment element down to the proximal ends of the extensions 406, which can be shortened towers. The external rod can be positioned adjacent to an outside surface of the patient's skin, thereby avoiding the need for a full length incision in the patient's back.

In any embodiments disclosed herein, the sixth guiding member 430 can have a greater degree of curvature, bending, or offset than the fifth guiding element 428. The fifth guiding member 428 can have a greater degree of curvature, bending, or offset than the fourth guiding element 426. The fourth guiding member 426 can have a greater degree of curvature, bending, or offset than the third guiding element 424. The third guiding member 424 can have a greater degree of curvature, bending, or offset than the second guiding element 422. The second guiding member 422 can have a greater degree of curvature, bending, or offset than the first guiding element 420. In any embodiments disclosed herein, the first guiding element 420 can be straight.

After the extensions 406 have been aligned by the alignment element as described above, then the final rod (not shown) can be advanced into all of the extensions 406. The final rod can be generally straight in a lateral direction, but have a curvature in the sagittal plane that generally matches a curvature of the patient's spine in the sagittal plane. The final rod can be inserted in a standard way, from the sides of the extensions as opposed to the top of the extensions, for example through each of the openings or slots 440 of each of the extensions 406. For example and without limitation, the final rod can be inserted from either the top of the construct or the bottom of the construct. In this manner, the leading end of the final rod will pass successively through each of the extensions 406. The final rod can then be advanced toward the screw heads 404 of each of the screws 402. This can avoid the need for the need for a full length incision in the patient's back, instead using only stab incisions at each extension 406. By approximately aligning the extensions 406 with the external rod, in some embodiments, it can be easier to advance the final rod into all of the extensions 406 and screw heads 404. Thereafter, a cap 460 (as shown in FIGS. 14A-14C) can be advanced down each of the extensions 406 and into engagement with the screw heads 404.

Figure 15:
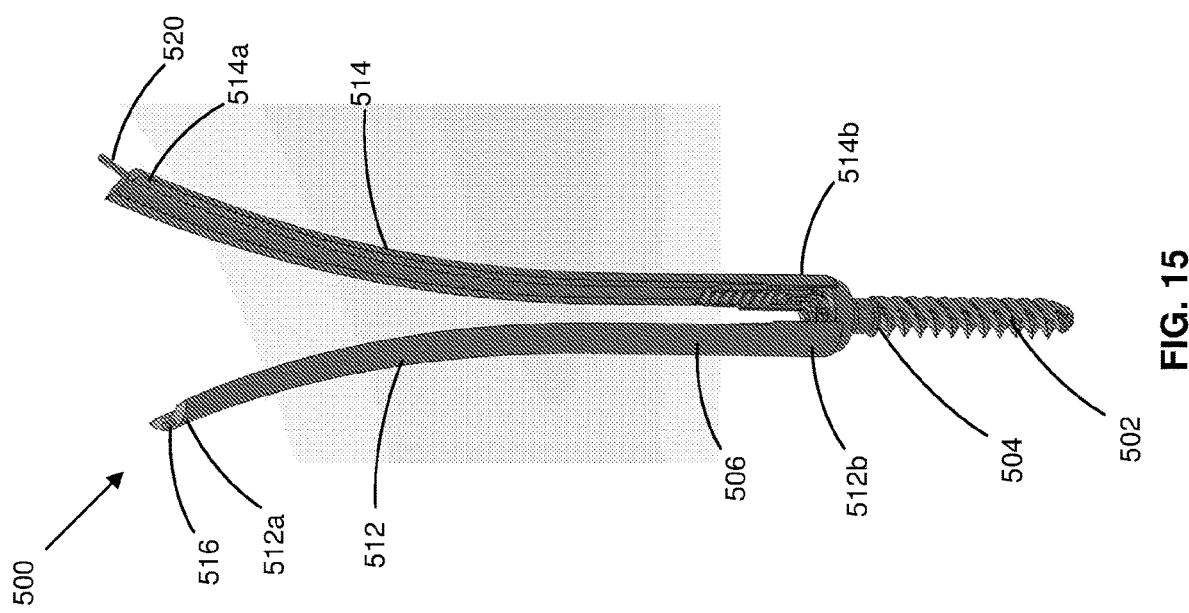
FIG. 15 is an isometric view of another embodiment of a device for treating a lateral curvature of the spine.

FIG. 15 is an isometric view of another embodiment of a device 500 for treating a lateral curvature of the spine. Any embodiments of the device 500 can be used with any of the embodiments of any of the systems and/or methods disclosed herein. Further, any embodiments of the device 500 can have any of the features, components, or other details of any other devices, systems or methods disclosed herein for treating a lateral curvature of the spine, in addition to or in combination with any of the features, components, or other details of any of the embodiments of the device 500 disclosed herein. Similarly, any of the other embodiments of the devices, systems, or methods disclosed herein for treating a lateral curvature of the spine can have any of the features, components or other details of any of the embodiments of the device 500 disclosed herein in place of or in combination with any of the features, components or other details thereof.

With reference to FIG. 15, the device 500 can have a screw 502, a screw head 504, and an extension 506 that can have a first guide 512 and a second guide 514. In this embodiment, the first guide 512 and the second guide 514 can diverge outwardly away from a centerline axis of the device 500. For example and without limitation, some embodiments of the device can have a first guide 512 that curves outwardly and a second guide 514 that curves outwardly from the centerline axis of the device 500, or a first guide 512 that bends outwardly and a second guide 514 that bends outwardly from the centerline axis of the device 500, or a first guide 512 that deflects outwardly and a second guide 514 that deflects outwardly from the centerline axis of the device 500. In any embodiments, the first guide 512 can have a proximal end portion 512*a* that is offset from the centerline axis of the device more than the distal end portion 512*b* of the first guide 512. Similarly, the second guide 514 can have a proximal end portion 514*a* that is offset from the centerline axis of the device more than the distal end portion 514*b* of the second guide 514.

Because the proximal end of the extension 506 has a wide opening therein, it will be easier to capture the rod in the case of a deformed curvature. As the rod (not shown) is lowered, the inside surface of the first and second guides 512, 514 will force the rod into the seat of the pedicle screw coupled with the extension 506. Further, any embodiments of the guides 512, 514 can have an opening 516 formed therein along an entire length of the guides 512, 514 for advancing the guides 512, 514 over a wire 520 that can be coupled with the screw 502 or screw head 504.

Figure 16:
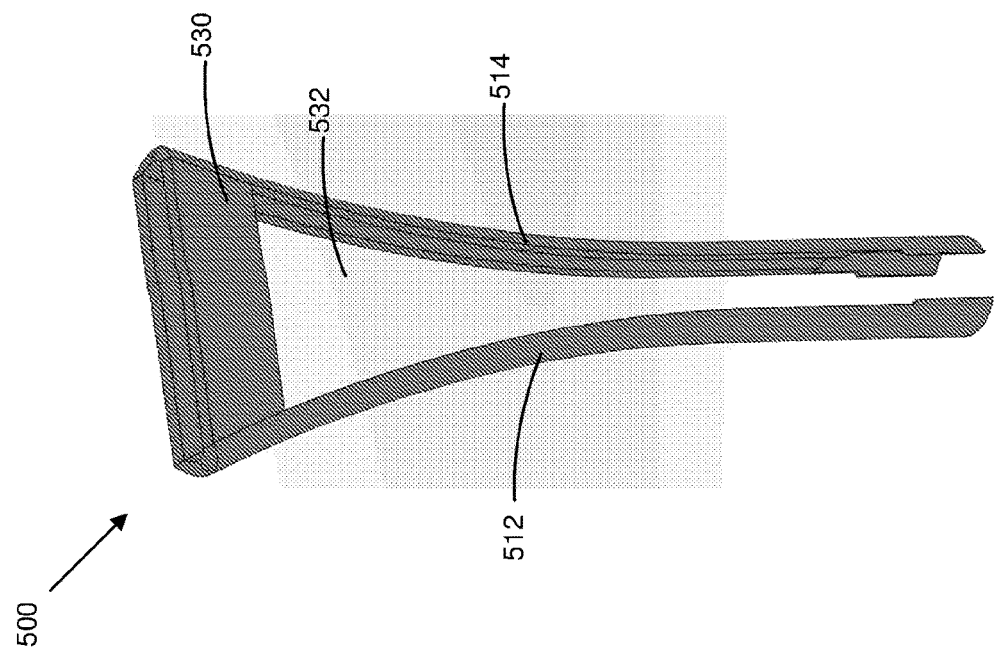
FIG. 16 is an isometric view of another embodiment of a device for treating a lateral curvature of the spine.

In some embodiments, the extension 506 can be closed at the top. For example and without limitation, as shown in FIG. 16, and embodiments of the device 500 can have a proximal end connector 530 configured to couple a proximal end of the guides 512, 514 together to increase the stiffness of the first and second guides 512, 514 and the extension 506 as a whole. In some embodiments, the connector 530 can be removably coupled with the proximal end portions of the guides 512, 514, or can be nonremovably coupled with proximal end portions of the guides 512, 514. The rod can be passed through the space 532 between the first and second guides 512, 514, under the connector 530 or before the connected 530 has been coupled with the guides 512, 514.

Any of the embodiments of the systems disclosed herein can have a plurality of devices 500, wherein a plurality of the devices 500 have a different curvature of the first and second guides or otherwise have a different width between the proximal portions of the first and second guides, to accommodate a spine with a differing level of lateral deformation. For example and without limitation, any embodiments of the system can include a first extension having a first width between a proximal portion of the first and the second sides of the first extension, a second extension having a second width between a proximal portion of the first and the second sides of the second extension, a third extension having a third width between a proximal portion of the first and the second sides of the third extension, a fourth extension having a fourth width between a proximal portion of the first and the second sides of the fourth extension, a fifth extension having a fifth width between a proximal portion of the first and the second sides of the fifth extension, and/or a sixth extension having a sixth width between a proximal portion of the first and the second sides of the sixth extension. The sixth width can be greater than the fifth width, the fifth width can be greater than the fourth width, the fourth width can be greater than the third width, the third width can be greater than the second width, and/or the second width can be greater than the first width.

The first and/or second guides of any of the first, second, third, fourth, fifth, sixth extensions and/or other extensions of the system can have straight trajectories, curved trajectories, bent trajectories, or otherwise offset trajectories wherein a distal end portion of the guiding member (i.e., the end portion closest to the screw head) is in a more narrow lateral position as compared to a proximal end portion of the guide when the extensions and the other components of the system are in an operable position in a patient's body.

While certain embodiments of the systems, devices, and methods for treating a lateral curvature of the spine have been described, these embodiments have been presented by way of example only, and are not intended to limit the scope of the disclosure. Indeed, the novel methods, devices, and systems described herein may be embodied in a variety of other forms. Furthermore, various omissions, substitutions and changes in the systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A system for treating at least a lateral curvature of a spine in the coronal plane, comprising:
    a plurality of screws each configured to be implanted in a corresponding one of a plurality of vertebrae, each of the plurality of screws having a screw head;
    a plurality of rigid extensions each configured to be removably coupled with a corresponding one of the plurality of screws, each of the plurality of rigid extensions having a proximal end portion, a distal end portion configured to be removably coupled with the screw head of a corresponding screw, and a middle portion between the proximal end portion and the distal end portion; and
    a rod that is configured to be coupled with each screw head of the plurality of screws;
    wherein:
        each of the plurality of rigid extensions has a length extending from the proximal end portion to the distal end portion;
        an angle of an axial centerline of the proximal end portion of at least one of the plurality of rigid extensions is different than an angle of an axial centerline of the distal end portion of the at least one of the plurality of rigid extensions;
        in an operable position, wherein the plurality of rigid extensions are each coupled with the plurality of screws, the axial centerline of the distal end portion of each of the plurality of rigid extensions extends from the respective one of the plurality of screws in a lateral direction relative to a longitudinal direction of the spine from the corresponding one of the plurality of vertebrae; and
        the system is configured such that the rod can be guided along the plurality of rigid extensions from the proximal end portion of each of the plurality of rigid extensions toward the distal end portion of each of the plurality of rigid extensions and into engagement with the plurality of screws.

2. The system of claim 1, wherein at least the middle portion of the plurality of extensions are curved.

3. The system of claim 1, wherein at least the middle portion of the plurality of extensions are bent.

4. The system of claim 1, wherein the angle of the axial centerline of the proximal end portion relative to the axial centerline of the distal end portion of at least one of the plurality of extensions is adjustable by a robot during a procedure to treat at least the lateral curvature of the spine.

5. The system of claim 1, wherein the system is configured to move one or more vertebra at least in a lateral direction in the coronal plane as the rod is advanced toward the distal end portion of each of the plurality of extensions and into engagement with each screw head of the plurality of screws.

6. The system of claim 1, wherein the system is configured to at least move one or more vertebra toward a lateral centerline of the spine as the rod is advanced toward the distal end portion of each of the plurality of extensions.

7. The system of claim 1, wherein the rod is generally straight in at least a lateral direction when the rod is in a pre-implanted state.

8. The system of claim 1, wherein the plurality of extensions have varying curvatures such that a curvature of a first of the plurality of extensions is different than a curvature of a second of the plurality of extensions.

9. The system of claim 1, wherein each of the plurality of extensions has a slot therein extending from the proximal end portion toward the distal end portion of each of the plurality of extensions, wherein the slot of each of the plurality of extensions is configured to slidably receive the rod therein such that the rod can be guided toward each screw head of the plurality of screws through each slot of the plurality of extensions.

10. The system of claim 9, further comprising a plurality of push elements configured to be advanced along the slot between the proximal and distal end portions of each of the plurality of extensions.

11. A system for treating a lateral curvature of a spine, comprising:
a plurality of screws each configured to be implanted in a corresponding one of a plurality of vertebrae, each of the plurality of screws having a screw head; and
a plurality of rigid extensions each configured to be removably coupled with a corresponding one of the plurality of screws, each of the plurality of extensions having a proximal end portion, a distal end portion configured to be removably coupled with the screw head of a corresponding screw, and a middle portion between the proximal end portion and the distal end portion;
wherein:
a proximal end portion of a first extension of the plurality of extensions is laterally spaced apart from a distal end portion of the first extension by a first distance when the first extension is coupled with a first vertebra in an operable position;
a proximal end portion of a second extension of the plurality of extensions is laterally spaced apart from a distal end portion of the second extension by a second distance when the second extension is coupled with a second vertebra in an operable position; and
the system is configured such that a rod can be guided along the plurality of rigid extensions from the proximal end portion of each of the
the second distance is greater than the first distance.

12. The system of claim 11, wherein a proximal end portion of a third extension of the plurality of extensions is laterally spaced apart from a distal end portion of the third extension by a third distance when the third extension is coupled with a third vertebra in an operable position, and the third distance is greater than the second distance.

13. The system of claim 11, wherein two or more of the plurality of extensions are non-linear between the proximal and distal end portions thereof.

14. The system of claim 11, wherein two or more of the plurality of extensions are curved or bent between the proximal and distal end portions thereof.

15. The system of claim 11, wherein at least the middle portion of the plurality of extensions are curved, bent, and/or angled.

16. The system of claim 11, further comprising a rod that is configured to be coupled with each screw head of the plurality of screws, wherein the system is configured to move one or more vertebra in at least a lateral direction as the rod is advanced toward the distal end portion of each of the plurality of extensions and into engagement with the screw head of each of the plurality of screws.

17. The system of claim 16, wherein the system is configured such that the rod can be simultaneously advanced down the plurality of extensions by incrementally advancing the rod toward the distal end portion of each of the plurality of extensions.

18. The system of claim 16, wherein the rod is generally straight in at least a lateral direction when the rod is in a pre-implanted state.

19. The system of claim 11, wherein each of the plurality of extensions has a slot therein extending from the proximal end portion toward the distal end portion of each of the plurality of extensions, wherein the slot of each of the plurality of extensions is configured to slidably receive a rod therein such that the rod can be guided toward each screw head of the plurality of screws through the slot of each of the plurality of extensions.

20. The system of claim 11, wherein each of the plurality of extensions is rigid along a length thereof.

21. A system for correcting at least a lateral curvature of a spine in the coronal plane, comprising:
a plurality of screws configured to be implanted in a plurality of vertebrae, each of the plurality of screws having a screw head;
a plurality of rigid extensions configured to be removably coupled with the plurality of screws, each of the plurality of extensions having a proximal end and a distal end configured to be removably coupled with the screw head of each of the plurality of screws, wherein the plurality of extensions are curved or bent along at least a portion thereof such that the proximal ends of the plurality of extensions extend at a nonzero angle relative to the distal ends of the plurality of extensions; and
a rod that is configured to be coupled with each screw head of the plurality of screws;
wherein:
a first extension of the plurality of rigid extensions has a different overall length than a second of the plurality of rigid extensions;
the proximal end of the first extension extends at a first nonzero angle relative to the distal end of the first extension and the proximal end of the second extension extends at a second nonzero angle relative to the distal end of the second extension;
the first nonzero angle is different than the second nonzero angle; and
the system is configured such that the rod can be guided along the plurality of rigid extensions from the proximal end of each of the plurality of rigid extensions toward the distal end of each of the plurality of rigid extensions and into engagement with the plurality of screws.

22. The system of claim 21, wherein the system is configured to move one or more vertebra in at least a lateral direction as the rod is advanced toward the distal end of each of the plurality of curved or bent extensions and into engagement with each screw head of the plurality of screws.

23. The system of claim 21, wherein the system is configured such that the rod can be simultaneously advanced down the plurality of curved or bent extensions by incrementally advancing the rod toward the distal end of each of the plurality of curved or bent extensions.

24. The system of any of claim 21, wherein the system is configured to at least move one or more vertebra toward a lateral centerline of the spine as the rod is advanced toward the distal end of each of the plurality of curved or bent extensions.

25. The system of claim 21, wherein the rod is generally straight in the lateral direction when the rod is in a pre-implanted state.

26. The system of claim 21, wherein the plurality of curved or bent extensions have varying lengths.

27. The system of claim 21, wherein the plurality of curved or bent extensions have varying curvatures.

28. The system of claim 21, wherein each of the plurality of curved or bent extensions has a slot therein extending from the proximal end of each of the plurality of curved or bent extensions toward the distal end of each of the plurality of curved or bent extensions, wherein the slot of each of the plurality of curved or bent extensions is configured to slidably receive the rod therein such that the rod can be guided toward each screw head of the plurality of screwsheads using the slot of each of the plurality of curved or bent extensions.

29. The system of claim 21, wherein:
the plurality of screws comprises a first plurality of screws and a second plurality of screws;
the system is configured such that the first plurality of screws will each be implanted in a plurality of vertebrae adjacent to each of the second plurality of screws;
the plurality of curved or bent extensions comprises a first plurality of curved or bent extensions and a second plurality of curved or bent extensions;
each of the first plurality of curved or bent extensions is configured to be removably coupled with the screw head of each of the first plurality of screws;
the rod is a first rod and the system comprises a second rod; and
the system is configured such that the first rod is guidable along the first plurality of curved or bent extensions from the proximal end of each of the first plurality of curved or bent extensions toward the distal end of each of the first plurality of curved or bent extensions and into engagement with the first plurality of screws, and such that the second rod is guidable along the second plurality of curved or bent extensions from the proximal end of each of the second plurality of curved or bent extensions toward the distal end of each of the second plurality of curved or bent extensions and into engagement with the second plurality of screws.

* * * * *

UNITED STATES PATENT AND TRADEMARK OFFICE
CERTIFICATE OF CORRECTION

PATENT NO. : 12,268,422 B2
APPLICATION NO. : 17/779975
DATED : April 8, 2025
INVENTOR(S) : Sherwin Hua Page 1 of 2

It is certified that error appears in the above-identified patent and that said Letters Patent is hereby corrected as shown below:

On the Title Page

Page 2, Column 2 item (56) (U.S. Patent Documents), Line 1, delete "Ardja et al." and insert -- Sutardja et al. --.

Page 3, Column 2 item (56) (U.S. Patent Documents), Line 11, insert -- 2006/0122597 A1 6/2006 Jones et al. --.

Page 4, Column 1 item (56) (U.S. Patent Documents), Line 23, insert -- 2010/0004695 A1 1/2010 Stad et al. --.

Page 4, Column 1 item (56) (U.S. Patent Documents), Line 26, insert -- 2010/0168803 A1 7/2010 Hestad et al. --.

Page 4, Column 1 item (56) (U.S. Patent Documents), Line 47, insert -- 2012/0316609 A1 12/2012 Wall et al. --.

Page 4, Column 1 item (56) (U.S. Patent Documents), Line 70, insert -- 2018/0036037 A1 2/2018 Abell et al. --.

In the Specification

Column 2, Line 34, delete "Deviren V. Xu" and insert -- Deviren V, Xu --.

Column 16, Line 58, delete "predictable manner Both" and insert -- predictable manner. Both --.

Column 26, Line nos. 11-12, delete "and programmed Additionally," and insert -- and programmed. Additionally, --.

Signed and Sealed this
Twenty-seventh Day of May, 2025

Coke Morgan Stewart
*Acting Director of the United States Patent and Trademark Office*

In the Claims

Column 33, Claim 11, Line 49, delete "of the" and insert -- of the plurality of rigid extensions toward the distal end portion of each of the plurality of rigid extensions into engagement with the plurality of screws; --.